(12) United States Patent
Mostafa et al.

(10) Patent No.: US 11,505,527 B1
(45) Date of Patent: *Nov. 22, 2022

(54) TETRAHYDROQUINOLINE DERIVATIVES AND A PROCESS OF PREPARATION THEREOF

(71) Applicant: King Abdulaziz University, Jeddah (SA)

(72) Inventors: Mohamed Mostafa, Jeddah (SA); Tamer Said Sayed Saleh, Jeddah (SA); Nesreen Said Ismael Ahmed, Jeddah (SA); Khadijah Saad Said Alghamdi, Jeddah (SA); Dina Abed Bakhotmah, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/826,894

(22) Filed: May 27, 2022

Related U.S. Application Data

(63) Continuation of application No. 17/577,217, filed on Jan. 17, 2022.

(51) Int. Cl.
*C07D 215/54* (2006.01)
*C07D 215/38* (2006.01)

(52) U.S. Cl.
CPC .......... *C07D 215/54* (2013.01); *C07D 215/38* (2013.01)

(58) Field of Classification Search
CPC .................... C07D 215/54; C07D 215/38
See application file for complete search history.

(56) References Cited

U.S. PATENT DOCUMENTS 6,387,929 B1 * 5/2002 Stoltefuss ............ C07D 409/04 546/14
6,958,346 B2 * 10/2005 Stoltefuss ............ C07D 401/04 546/15

* cited by examiner

*Primary Examiner* — D Margaret M Seaman
(74) *Attorney, Agent, or Firm* — WCF IP

(57) ABSTRACT

The present disclosure provides tetrahydroquinoline derivatives of Formula (I)

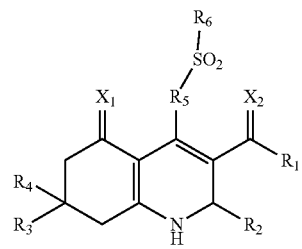

Formula (I)

wherein $X_1$ and $X_2$ each, independently, are oxygen or sulphur; $R_1$ is a lower alkoxy, or an optionally substituted aryl group; $R_2$ is selected from a group consisting of hydrogen, lower alkyl, haloalkyl, or an amino group; $R_3$ and $R_4$ each, independently, are hydrogen, or lower alkyl groups; and R5 and R6 are optionally substituted aryl groups. The present disclosure also provides a method for making the compound of Formula (I).

12 Claims, 27 Drawing Sheets

Farnesyl transferase inhibitor
(Tipifarnib)™

Maxi-K channel opener p38αMAP Kinase inhibitor

Adensine A$_{2B}$ antagonist

TETRAHYDROQUINOLINE DERIVATIVES AND A PROCESS OF PREPARATION THEREOF

TECHNICAL FIELD

The present disclosure relates to receptor tyrosine kinase (RTK) inhibitors, and more specifically, the present disclosure relates to derivatives of tetrahydroquinolines having an inhibitory activity against RTK, and a method for preparing the same.

BACKGROUND

Breast cancer is one of the most common causes that threatens women's health all over the world. Studies have shown that breast cancer impacts about 15% of all cancer deaths occurring in women. The incidence of breast cancer is increasing globally, and it is reported that one in eight women are diagnosed with breast cancer during their lifetime.

Receptor tyrosine kinases (RTKs) are considered as successful molecular targets for various anticancer therapies. They are composed of many triggered domains when a ligand binds to their extracellular regions, activating signalling cascades downstream. RTKs such as, epidermal growth factor receptor (EGFR), vascular endothelial growth factor receptor-2 (VEGFR-2), and platelet-derived growth factor receptor (PDGFR) play crucial roles in controlling multiple cellular processes, including cell proliferation, differentiation, survival, and apoptosis. Mutations or deletions in gene functions can result in uncontrolled expression of protein kinases, which can lead to tumour development, angiogenesis, and metastasis. Therefore, RTKs are considered novel drug targets to develop tyrosine kinase inhibitors. Tyrosine kinase inhibitors/suppressors reduce or suppress the overexpression of tyrosine kinase and maintain its physiological balance.

Conventionally used RTK inhibitors for treatment of cancer; suffer from drawbacks like drug-induced toxicity to normal cells and drug-resistance. Therefore, there exists a need to develop more selective and safer anti-cancer agents that overcome the limitations of the prior art.

SUMMARY

The present disclosure provides tetrahydroquinoline derivatives having an inhibitory activity against RTK's.

In an aspect, the present disclosure provides a compound of Formula (I) and isomers and pharmaceutically acceptable salts thereof.

Formula (I)

wherein $X_1$ and $X_2$ each, independently, are oxygen or sulphur; $R_1$ is a lower alkoxy, or an optionally substituted aryl group; $R_2$ is selected from a group consisting of hydrogen, lower alkyl, haloalkyl, or an amino group; $R_3$ and $R_4$ each, independently, are hydrogen, or lower alkyl groups; and R5 and R6 are optionally substituted aryl groups.

In an embodiment, $X_1$ and $X_2$ are oxygen.

In another embodiment, $R_1$ is a methoxy or an ethoxy group.

In an embodiment, $R_1$ is an aryl group substituted with at least one substituent selected from a group consisting of a lower alkyl, haloalkyl, and a halogen.

In an embodiment, $R_1$ is an aryl group substituted with a methyl group or a halogen. In an example, the halogen is bromine.

In an embodiment, each of $R_3$ and $R_4$ is methyl groups.

In an embodiment, $R_5$ is a phenyl group.

In an embodiment, $R_6$ is a phenyl or a tolyl group.

In an aspect, the present disclosure provides a compound of Formula (II) and isomers and pharmaceutically acceptable salts thereof:

Formula (II)

In an aspect, the present disclosure provides a pharmaceutical composition including the compound of Formula (I), and at least one pharmaceutically acceptable excipient selected from a group consisting of disintegrators, binders, fillers, lubricants, and any combination thereof.

The present disclosure also provides a method of making the compound of Formula (I). In an aspect, the method comprises sonicating a combination of dimedone, a substituted benzaldehyde, and a reactant comprising an active methylene group, in presence of a catalyst to obtain the compound of Formula (I).

In an embodiment, the reactant comprising the active methylene group is a compound of Formula (III).

Formula (III)

wherein, 'X' is an ester or a cyano group; $R_7$ is selected from a group consisting of lower alkyl, haloalkyl, and an optionally substituted aryl group.

In an embodiment, the 'X' is a methoxycarbonyl or an ethoxy carbonyl group.

In an embodiment, $R_7$ is a substituent selected from a group consisting of methyl, ethyl, trifluoromethyl, phenyl, tolyl and a bromophenyl group.

In an embodiment, the substituted benzaldehyde is 4-(phenylsulfonyl) benzaldehyde or 4-tosylbenzaldehyde.

In an embodiment, the catalyst is chitosan decorated copper nanoparticles (CS/CuNPs).

In an embodiment, the method includes sonicating the combination of dimedone, substituted benzaldehyde, and the reactant comprising the active methylene group, in presence of ammonium acetate and ethanol.

In an embodiment, the method includes sonicating a combination of dimedone, substituted benzaldehyde, and the reactant comprising the active methylene group at a frequency range of 20-40 Hz for a period of 20 to 30 minutes.

The foregoing as well as other features and advantages of the present disclosure will be more fully understood from the following description, examples, and claims.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
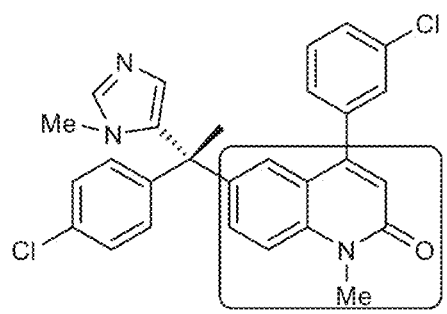
FIGS. 1A-1D shows examples of bioactive quinolines derivatives.
Figure 1B:
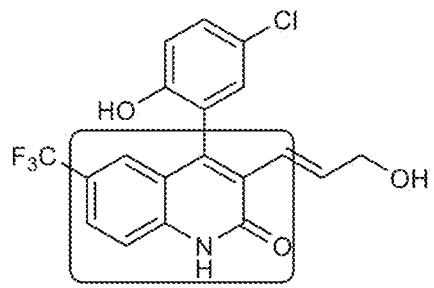
Figure 1C:
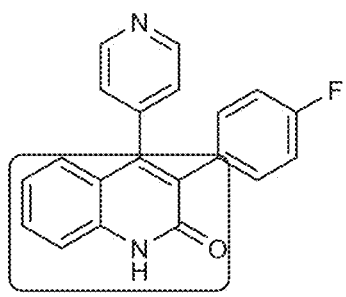
Figure 1D:
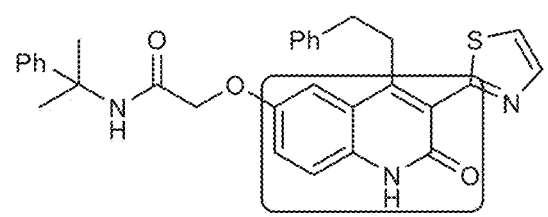

Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein, are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements. A skilled artisan will appreciate that various alternate embodiments and forms may be prepared. Examples, therefore, given are only for illustration purposes without any intention to restrict the embodiments to a given set of examples. Specific functional aspects are provided merely to enable a person skilled in the art to perform the invention and should not be construed as limitations of the invention. Any method steps and processes described herein are not to be construed as necessarily requiring their performance in the particular order discussed or illustrated, unless specifically identified as an order of performance It is also to be understood that additional or alternative steps may be employed, unless otherwise indicated.

The use of the singular herein includes the plural (and vice versa) unless specifically stated otherwise.

The use of the terms "include," "includes", "including," "have," "has," or "having," "comprise," "comprises," "comprising" or the like should be generally understood as open-ended and non-limiting unless specifically stated otherwise.

It is understood that the order of steps or order for performing certain actions can be changed so long as the intended result is obtained. Moreover, two or more steps or actions may be conducted simultaneously.

As used herein, the term "about" or "between" refers to a ±20% to ±10% variation from the nominal value unless otherwise indicated.

As used herein, the term "halogen" refers to fluorine, chlorine, bromine or iodine.

As used herein, the term "haloalkyl" refers to an alkyl radical having one or more hydrogen atoms replaced by a halogen atom.

As used herein, the term "alkyl group" or "alkyl" refers to a straight or branched saturated hydrocarbon chain having 1 to 20 carbon atoms and a cyclic saturated hydrocarbon chain having 3 to 10 carbon atoms. Examples of alkyl group include methyl, ethyl, propyl, isopropyl, butyl, sec-butyl, tert-butyl, pentyl, isopentyl, neopentyl, tert-pentyl, 1-methylbutyl, 2-methylbutyl, 3-methylbutyl, hexyl and isohexyl groups, and the like.

As used herein, the term "lower alkyl" refers to a branched or linear alkyl having from 1 to 4 carbon atoms. Examples include, but are not limited to, methyl, ethyl, propyl, isopropyl, isobutyl, and tertiary butyl.

The term "alkoxy group" or "alkoxy" refers to a straight or branched alkyloxy group having 1 to 10 carbon atoms and a cyclic alkyloxy group having 3 to 10 carbon atoms, more preferably as a straight or branched alkoxy group having 1 to 5 carbon atoms. Examples of alkoxy group include methoxy, ethoxy, propoxy, isopropoxy, butoxy, isobutoxy, tert-butoxy, pentoxy, isopentoxy, neopentoxy, tert-pentoxy, hexoxy and isohexoxy groups, and the like.

The term "tolyl" refers to a group derived from toluene by removal of a hydrogen atom.

As used herein, the term "aryl" refers to an organic radical derived from an aromatic hydrocarbon by removal of one hydrogen, such as phenyl or naphthyl. Aryl groups may be unsubstituted or substituted with 1 to about 4 substituents on the ring. Specific examples of substituents include: halo, cyano, alkyl, haloalkyl, phenyl, phenoxy or any combination thereof.

"The term 'optionally substituted' refers to a referenced group that may be substituted with one or more additional group(s) individually and independently selected from the listed groups.

As used herein, "pharmaceutically acceptable salts" refers to salts that are pharmaceutically acceptable and have the desired pharmacological properties. Suitable inorganic salts include, e.g., those formed with the alkali metals or alkaline earth metals, e.g. sodium, potassium, magnesium, calcium, aluminum. Pharmaceutically acceptable salts can also include acid addition salts formed from the reaction of basic moieties, such as amines, in the parent compound with inorganic acids (e.g., hydrochloric and hydrobromic acids) and organic acids (e.g., acetic acid, citric acid, maleic acid, propionic, lactic, tartaric, succinic, fumaric, maleic, malonic, mandelic, malic, phthalic, hydrochloric, hydrobromic, phosphoric, nitric, sulfuric, and the alkane- and arenesulfonic acids such as methanesulfonic acid and benzenesulfonic acid naphthalenesulfonic, toluenesulfonic, camphorsulfonic). Other suitable examples of pharmaceutically acceptable salts include, but are not limited, to sulfate; citrate, acetate; oxalate; chloride; bromide; iodide; nitrate; bisulfate; phosphate; acid phosphate; isonicotinate; lactate; salicylate; acid citrate; tartrate; oleate; tannate; pantothenate; bitartrate; ascorbate; succinate; maleate; gentisinate; fumarate; gluconate; glucaronate; saccharate; formate; benzoate; glutamate; methanesulfonate; ethanesulfonate; benzenesulfonate; p-toluenesulfonate; pamoate (i.e., 1,1'-methylene-bis-(2-hydroxy-3-naphthoate)); and salts of fatty acids such as caproate, laurate, myristate, palmitate, stearate, oleate, linoleate, and linolenate salts. Suitable organic salts also include, e.g., those formed with organic bases such as the amine bases, e.g., ethanolamine, diethanolamine, triethanolamine, tromethamine, N-methylglucamine, and the like, and those which can form N-tetraalkylammonium salts such as N-tetrabutylammonium salts.

Among heterocyclic compounds, quinoline scaffold has become an important construction motif for the development of new drugs. Quinoline and its derivatives have been reported to show significant anticancer activity through different mechanism of action such as growth inhibitors by cell cycle arrest, apoptosis, inhibition of angiogenesis, disruption of cell migration and modulation. Food and Drug Administration (FDA) has approved various quinoline small molecules inhibitors for clinical uses in cancer (FIG. 1A to FIG. 1D). [Kraus JM, Tatipaka HB et. al., J Med Chem. 2010; 53: 3887-3898; Hewawasam P, et. al., J Med Chem. 2003; 46: 2819-2822; Peifer C, et. al., Bioorg Med Chem Lett. 2008;18: 1431-1435; Kulagowski JJ, et. al., J Med Chem. 1994; 37:1402-1405; McGuinness BF, et. al., Bioorg Med Chem Lett. 2010;20: 7414-7420].

Figure 2:
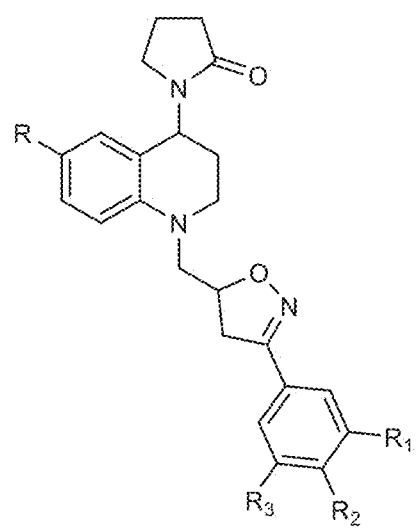
FIG. 2 shows a general markush structure covering tetrahydroquinoline-isooxazoline hybrid derivatives.

Referring to FIG. 2, a general Markush structure covering tetrahydroquinoline-isoxazoline hybrid derivatives is described. A series of tetrahydroquinoline-isoxazoline hybrid derivatives synthesized as described in Bernal CC, et. Al., *Medicinal Chemistry Research*, 2020, 29, 675-689. These compounds have shown good anti-cancer effects and were found to induce apoptosis with good selectivity index.

Figure 3A:
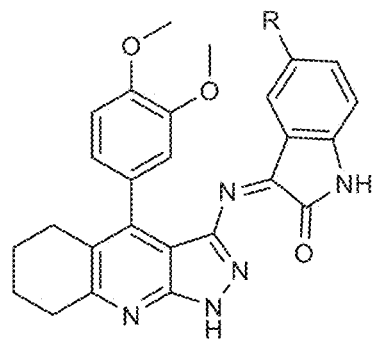
FIG. 3A and FIG. 3B shows tetrahydroquinoline derivatives having pyrazole and hydrazide moieties.
Figure 3B:
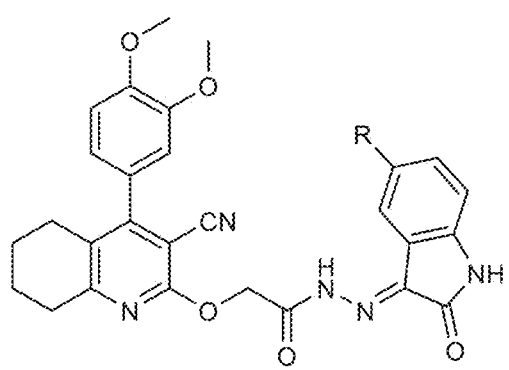

Referring to FIG. 3A and FIG. 3B, tetrahydroquinoline derivatives having pyrazol and hydrazide moieties are depicted [Fathy U, et. Al., *J Heterocyclic Chem.*, 2020, 57, 2108-20110]. The compounds were examined in vitro for their cytotoxic activity against HepG-2 and A549 cancer cells. Promising activity was observed with these compounds as anticancer agents against HepG-2 and A549 cancer cells.

Figure 4A:
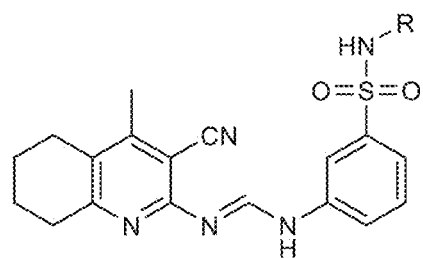
FIG. 4A and FIG. 4B show a general structure covering quinoline and pyrimido [4,5-b] quinoline derivatives bearing a substituted or unsubstituted sulfonamide moiety.
Figure 4B:
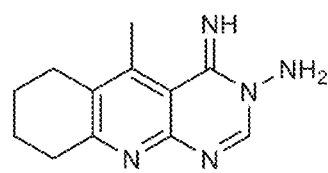

FIG. 4A and FIG. 4B shows a general structure covering quinoline and pyrimido[4,5-b]quinoline derivatives bearing a substituted or unsubstituted sulfonamide moiety [Ghorab MM, et. Al., *European Journal of Medicinal Chemistry*, 2009, 44, 4211-4217]. These compounds are carbonic anhydrase (CA) inhibitors, and were evaluated for their in vitro anticancer activity against breast cancer cell line (MCF7). The screened compounds showed interesting cytotoxic activities compared to a reference drug.

Figure 5A:
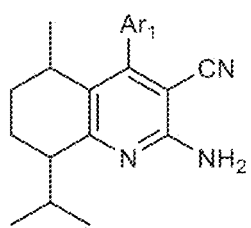
FIGS. 5A-5C shows a general structure covering a series of tetrahydroquinolines with different substituents at C-2 and C-4 positions.
Figure 5B:
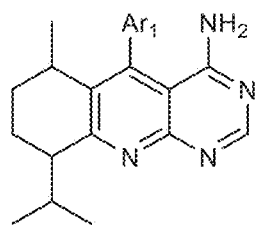
Figure 5C:
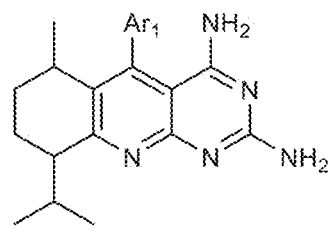

FIGS. 5A-5C shows a general structure covering a series of tetrahydroquinolines with different substituents at C-2 and C-4 positions in addition to several tetrahydropyrimidoquinolin-4-amines and tetrahydropyrimidoquinoline-2,4-diamines The synthesized compounds were evaluated for the in vitro anticancer activity against human colon carcinoma (HCT116) and human breast adenocarcinoma (MCF7) cell lines [Gedawy E M, Kassab A E, et. al. . . . , *Medicinal Chemistry Research*, 2015, 23, 3387-3397]. The compounds showed potent anticancer activity against both HCT116 and MCF-7 cell lines.

Figure 6:
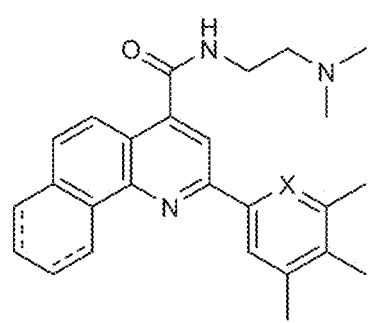
FIG. 6 shows a general structure covering a series of benzo- and tetrahydro benzo-[h]quinoline compounds bearing a flexible (dimethyl amino) ethyl carboxamide side chain as DNA intercalating antitumor agents.

FIG. 6 shows a general structure covering a series of benzo- and tetrahydro benzo-[h]quinoline compounds bearing a flexible (dimethylamino)ethylcarboxamide side chain as DNA intercalating antitumor agents [Jafari F, et. al., *European Journal of Medicinal Chemistry*, 2019, 164, 293-303]. The cytotoxic activity of the synthesized compounds was evaluated against four human cancer cell lines including MCF-7, A2780, C26 and A549. It was observed that saturated quinolines (tetrahydrobenzo[h]quinolines) exhibited more cytotoxicity compared to their corresponding unsaturated quinolines (benzo[h]quinolines).

Understanding the in vitro outcomes of compounds disclosed in FIG. 1 to FIG. 6 indicate that the anti-cancer activity was observed best with compounds having a branched cyclohexyl moiety fused to pyridine ring (as can be observed in FIG. 5). Also, it was observed that the substituent in quinoline derivatives at position 2 had a marked effect on the anticancer activity. Compounds with carbonyl or amino groups at 2-position were found to possess better anticancer activity.

Figure 7:
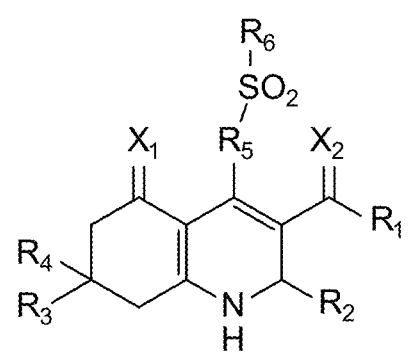
FIG. 7 is a markush structure depicting a compound (tetrahydroquinoline-phenylsulfonyl derivatives or tetrahydroquinolin-5(1H)-one derivatives) of Formula (I)

To bridge the gap between minimizing side effects and the mode of action of cytotoxic drugs, the present disclosure is directed towards design and synthesis of novel cytotoxic compounds, having a 4,6,7,8-tetrahydroquinolin-5(1H)-one scaffold. In an embodiment, the present disclosure includes a compound of Formula (I) and isomers and pharmaceutically acceptable salts thereof. The molecular structure of the compound of Formula (I) is provided in FIG. 7.

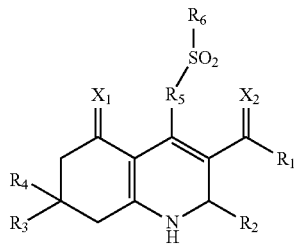

Formula (I)

wherein $X_1$ and $X_2$ each, independently, are oxygen or sulphur; $R_1$ is a lower alkoxy, or an optionally substituted aryl group; $R_2$ is selected from a group consisting of hydrogen, lower alkyl, haloalkyl, or an amino group; $R_3$ and $R_4$ each, independently, are hydrogen, or lower alkyl groups; and $R_5$ and $R_6$ are optionally substituted aryl groups.

In an embodiment, $X_1$ and $X_2$ are oxygen.
In another embodiment, $R_1$ is a methoxy or an ethoxy group.
In an embodiment, $R_1$ is an aryl group substituted with at least one substituent selected from a group consisting of a lower alkyl, haloalkyl, and a halogen.
In an embodiment, $R_1$ is an aryl group substituted with a methyl group or a halogen. In an example, the halogen is bromine.
In an embodiment, each of $R_3$ and $R_4$ is methyl groups.
In an embodiment, $R_5$ is a phenyl group.
In an embodiment, $R_6$ is a phenyl or a tolyl group.

A particularly preferred sub-class of the compound of Formula (I) or a pharmaceutically acceptable derivative or salts thereof is a compound of Formula (II).

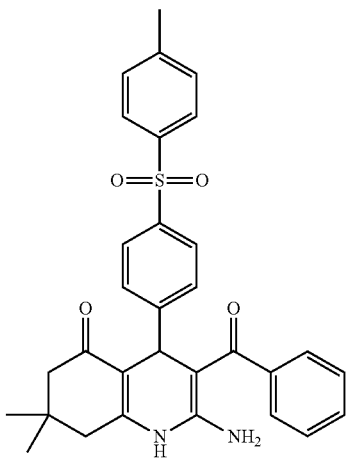

Formula (II)

The compound of Formula (I) along with a pharmaceutically acceptable excipient can be used for oral or parenteral administration. The pharmaceutically acceptable excipients include, for example, a binder (syrup, gum acacia, gelatin, sorbit, tragacanth, polyvinylpyrrolidone, and the like), an filler (lactose, sugar, cornstarch, potassium phosphate, sorbit, glycine, and the like), a lubricant (magnesium stearate, talc, polyethylene glycol, silica, and the like), and a disintegrant (potato starch, and the like).

Preferred pharmaceutical compositions for oral administration of the compound of Formula (I) include solid formulations such as tablets, granules, capsules or powders; and liquid formulations such as solutions, suspensions or emulsions.

The pharmaceutical compositions including the compound of Formula (I) can be used alone or in combination with other drugs useful for treatment of cancer.

In an embodiment, the present disclosure provides a method of treating a patient suffering from cancer comprising administering a therapeutically effective amount of a compound of Formula (I) or the pharmaceutically acceptable salts or hydrates thereof. In some embodiments the method of administering the therapeutically effective amount of a compound of Formula (I) is by oral administration. In certain other embodiments, the mode of administration is by intravenal (I.V) or by intramural (I.M) administration. In certain other embodiments, the mode of administration is topical administration containing the compound of Formula (I). The composition(s) may be also incorporated in a gel or matrix base for application in a patch, which would allow a controlled release of compound through a transdermal barrier. In an embodiment, the cancer may be lung cancer, prostate cancer, ovarian cancer, breast cancer, skin cancer, and sarcoma. In an embodiment, the cancer is breast cancer. In an embodiment, the patient is a human. In some embodiments, the patient is a woman The compounds of the present dislcsoure were found to enhance apoptosis in the human breast cancer (MCF-7), and also function as inhibitors of RTKs.

In an aspect, the present disclosure provides for method of making the compounds of Formula (I). The reaction scheme is provided in FIG. 8. The process involves the utilization of a heterogenous catalyst under ultrasonic irradiation to obtain high yields of the compound of Formula (I) in a short period. For this purpose, a mixture of dimedone (1) (1 mmol), different substituted aldehydes 2a, b (1 mmol), active methylene compounds 3a-f (1 mmol) and ammonium acetate (9 mmol) in ethanol (25 ml) containing a catalytic amount of Cu-chitosan nanoparticles (0.1 g) was refluxed at 60° C. for the appropriate time (20 to 30 minutes for ultrasound irradiation, and 5 to 6 hours under conventional reaction conditions) until completion of the reaction (monitored by TLC). The reaction mixture was filtered to separate the catalyst; further, the filtrate was cooled at room temperature, and the product obtained was filtered, dried, and purified by recrystallisation from ethanol. The synthesized 4,6,7,8-tetrahydroquinolin-5(1H)-one-based derivatives (4a to 4l) were examined for their potential as cytotoxic agents against MCF-7 cancer cells, in vitro, using MTT assay utilizing staurosporine as a standard drug. The compounds 4b, 4e, 4j, and 4k appeared as the most promising cytotoxic candidates. The safety profile for each of these compounds was evaluated as well, and it was observed that compounds 4b and 4j appeared as the safest agents on the normal cells. Compound 4j was found to have an inhibitory effect on RTK's.

Figure 8:
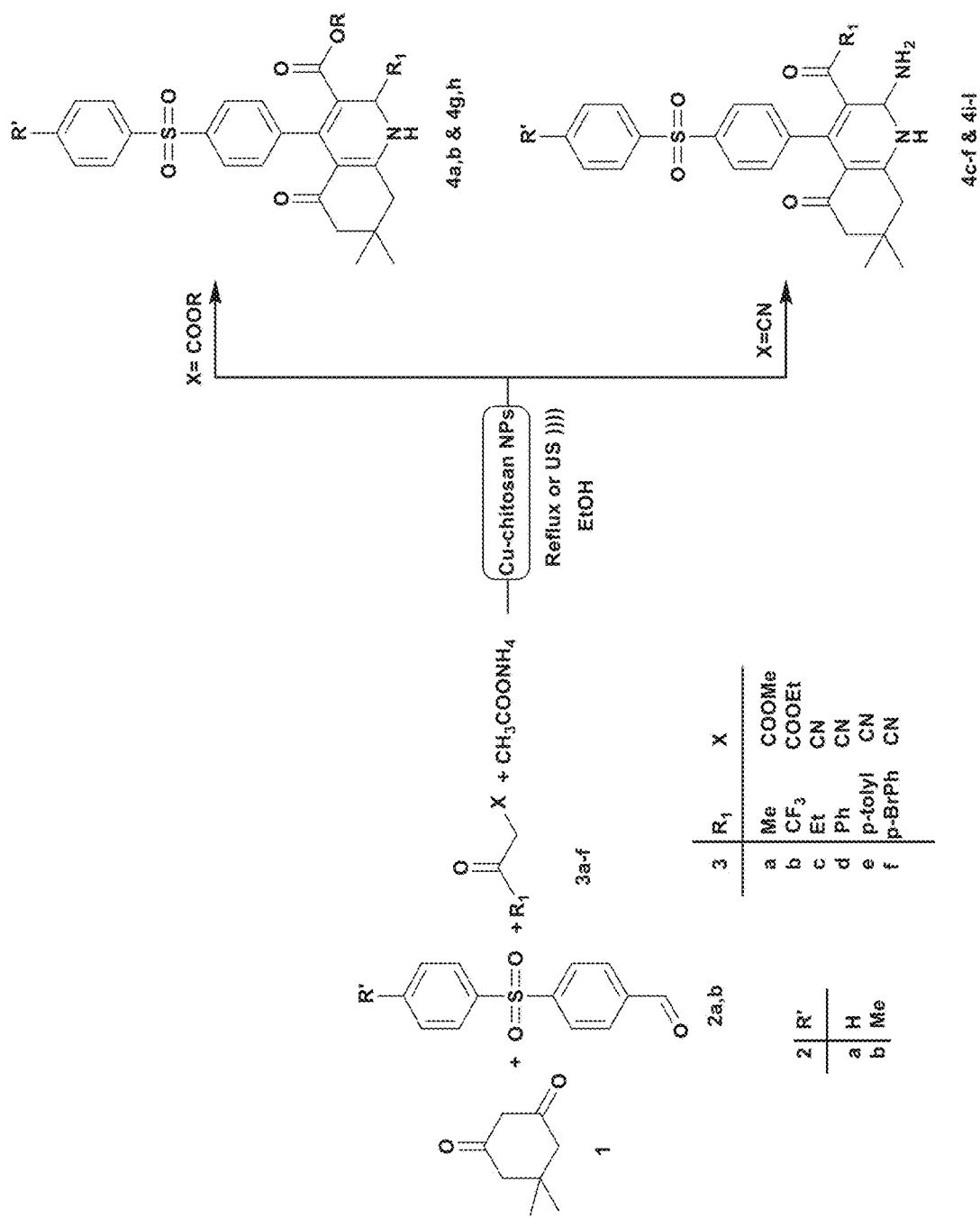
FIG. 8 is a schematic diagram depicting a method for preparing the compound of Formula (I)
Figure 9:
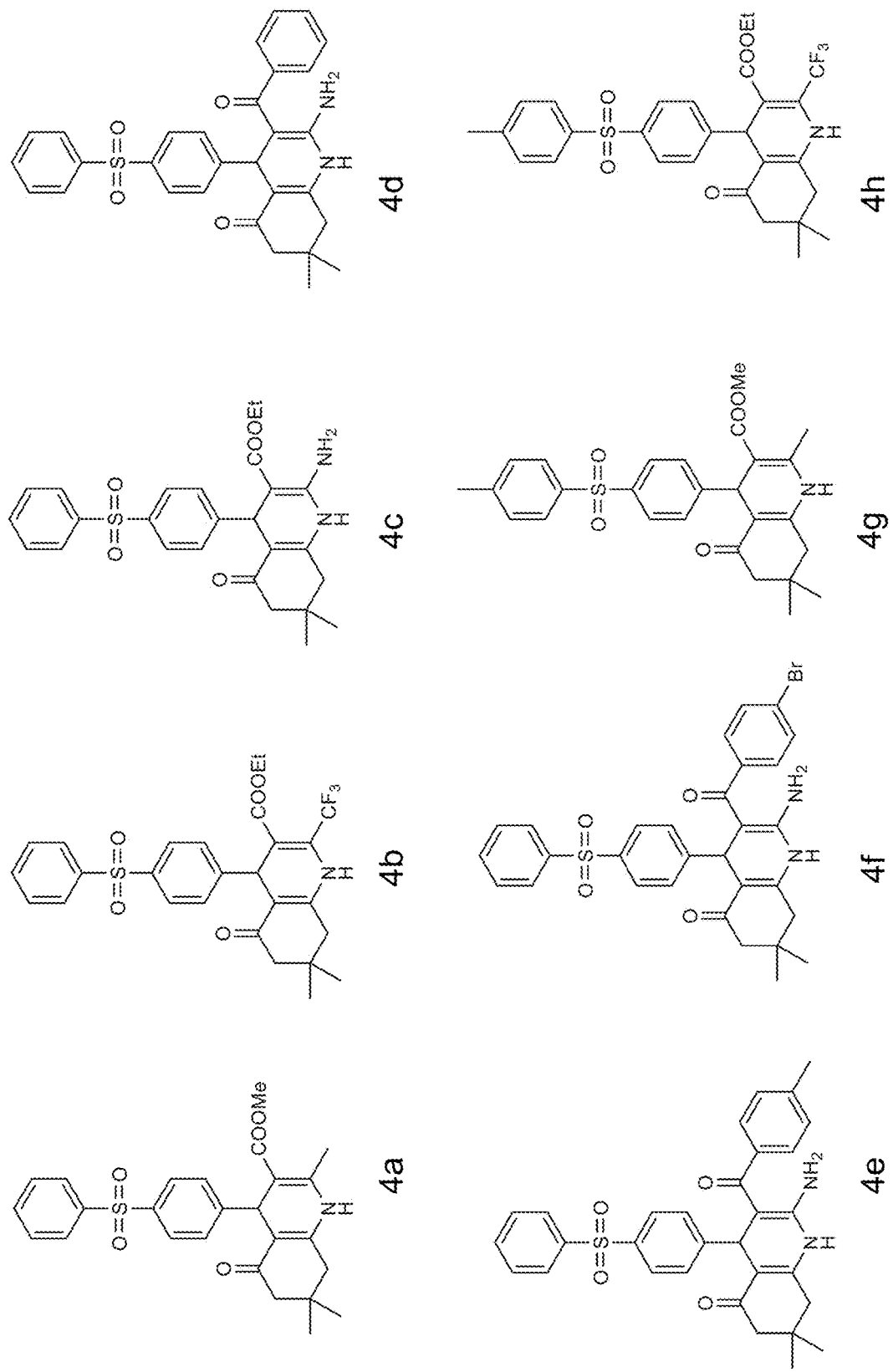
FIG. 9 shows molecular structures of compounds 4a to 4l having 4,6,7,8-tetrahydroquinolin-5(1H)-ones scaffold, as synthesized by the method of the present disclosure.
Figure 9:
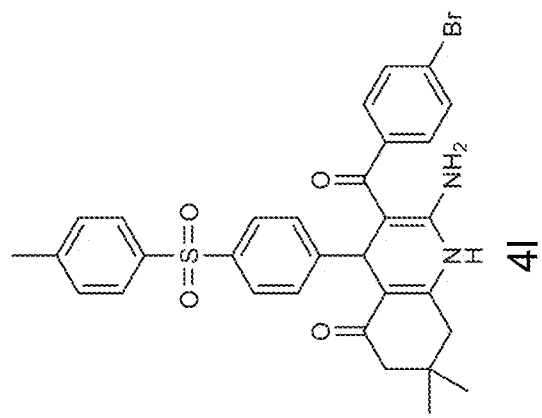
Figure 9:
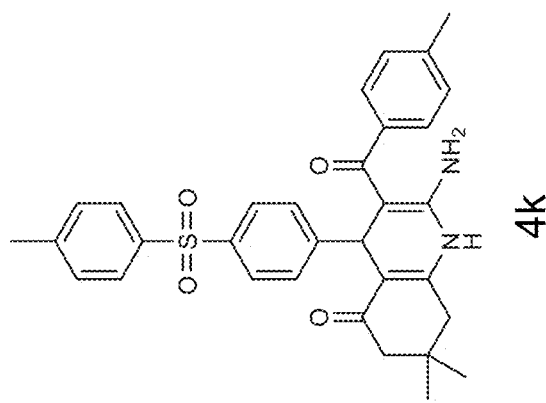
Figure 9:
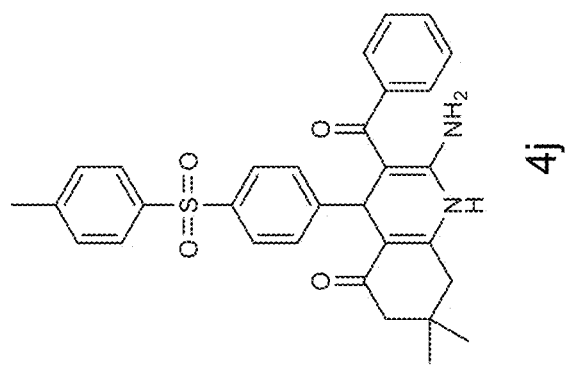
Figure 9:
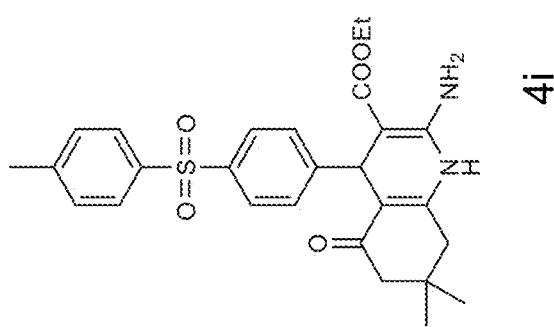
Figure 10A:
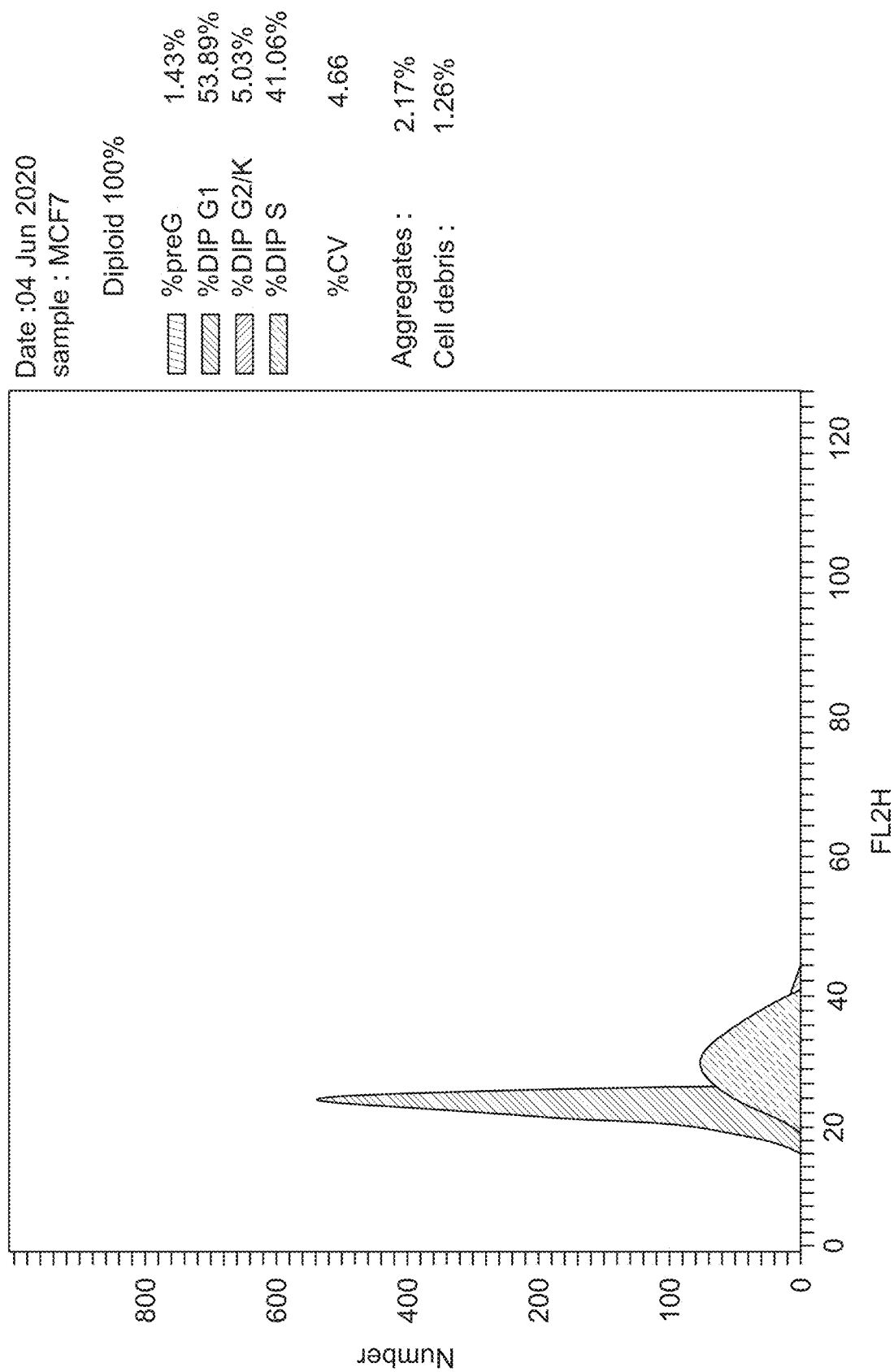
FIG. 10A to FIG. 10C, and FIG. 11A to FIG. 11C show apoptotic effects of compounds 4b and 4j against MCF-7 cells.
Figure 10B:
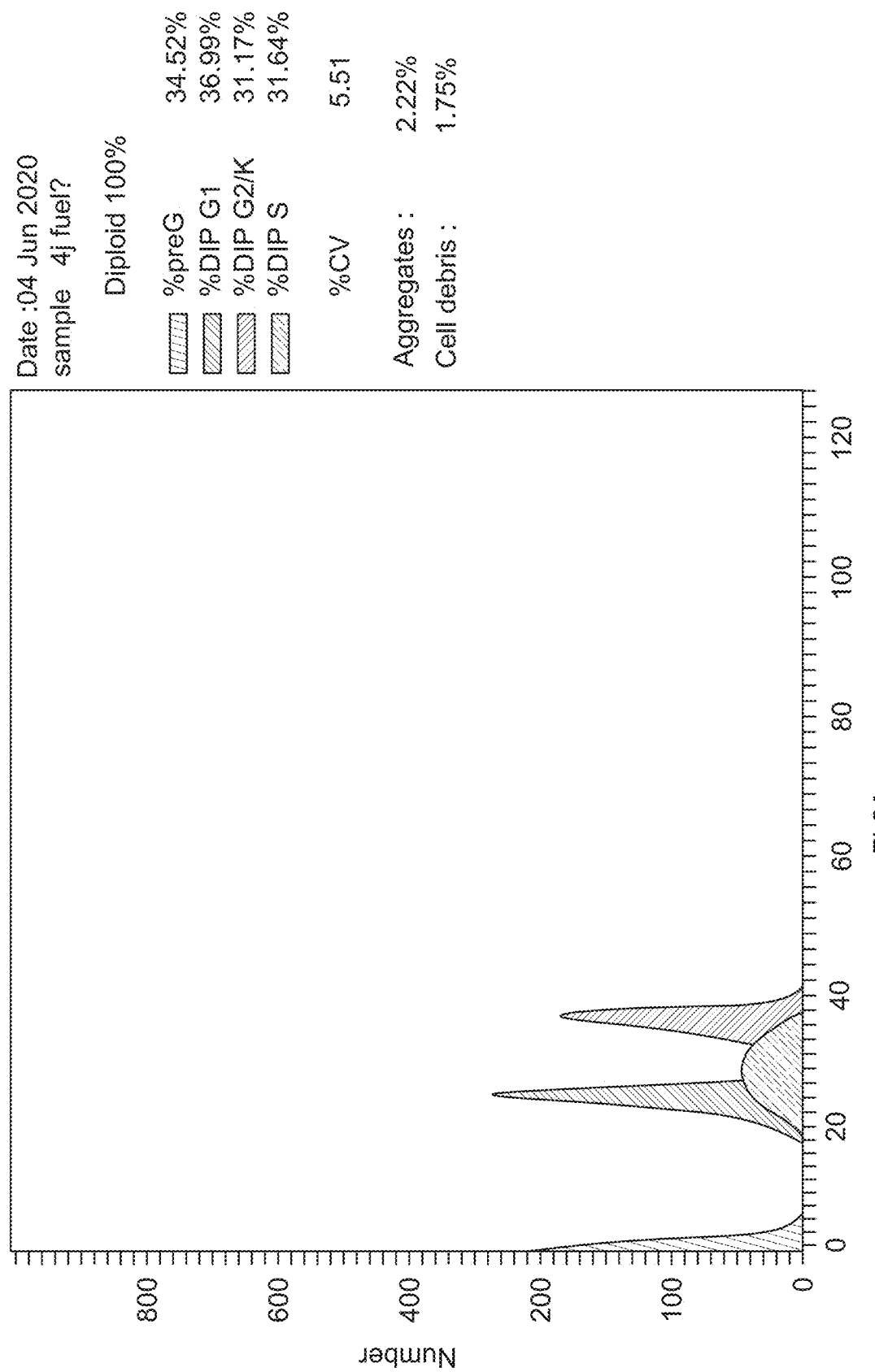
Figure 10C:
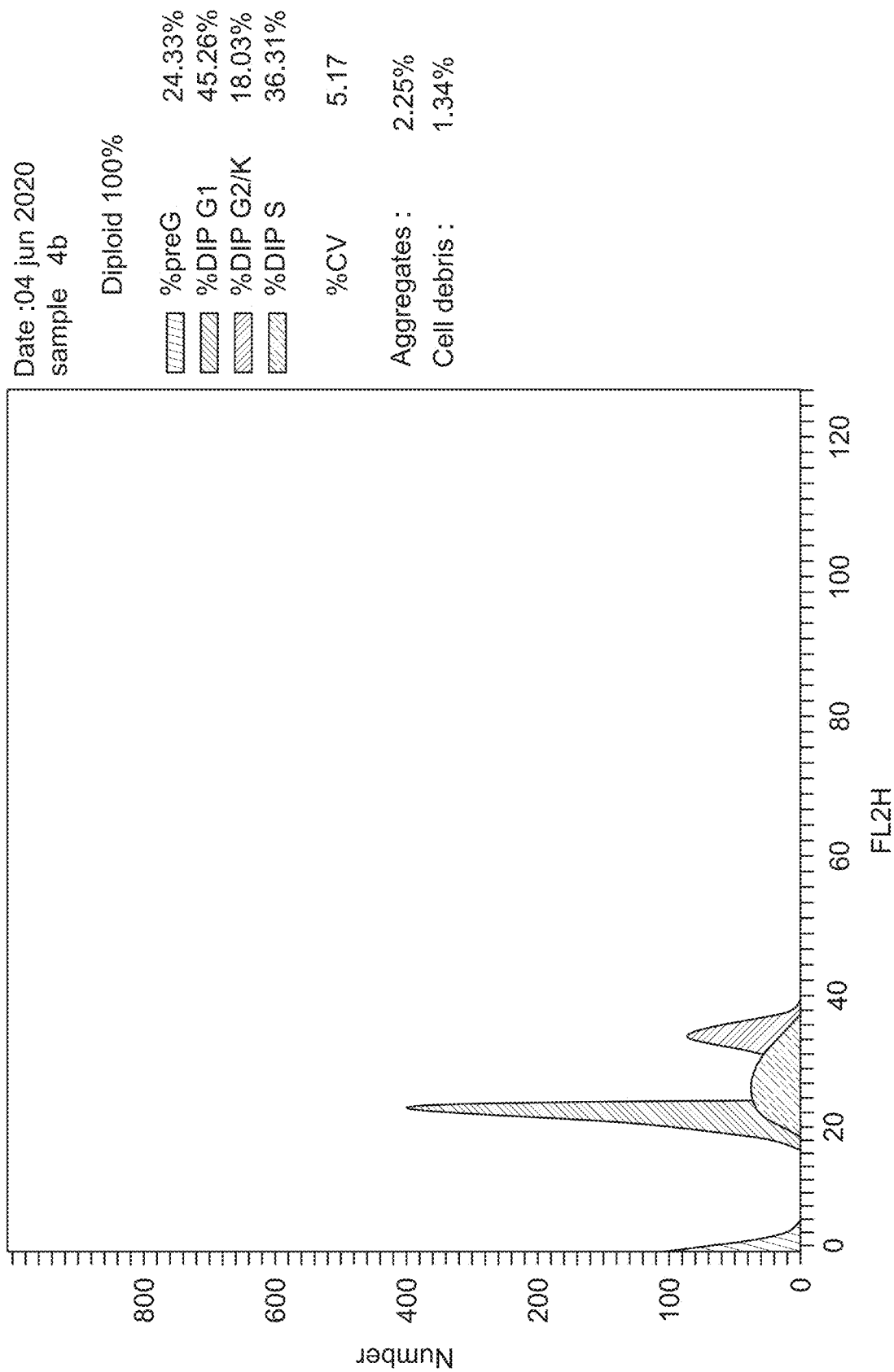
Figure 11A:
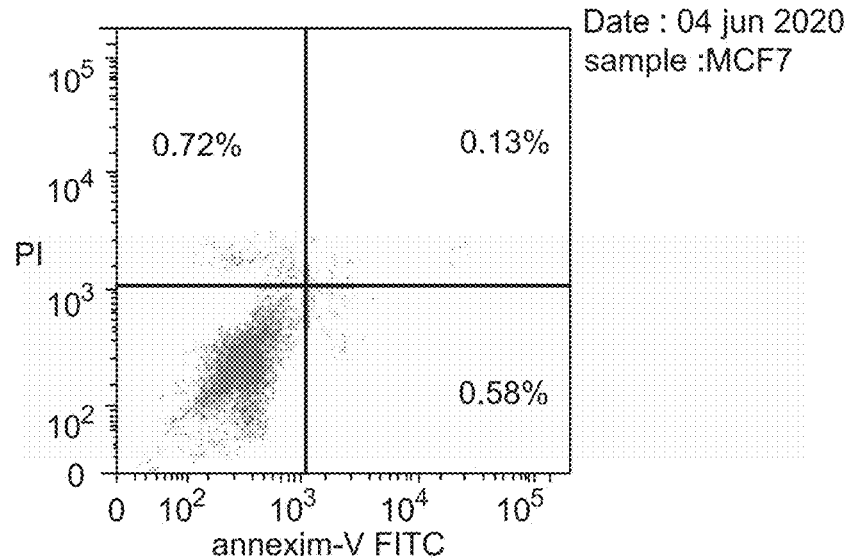
Figure 11B:
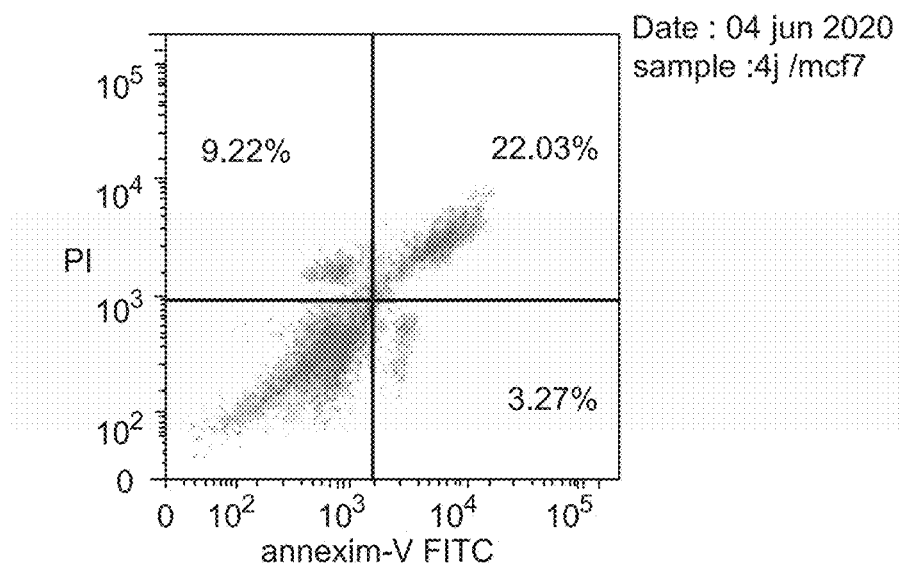
Figure 11C:
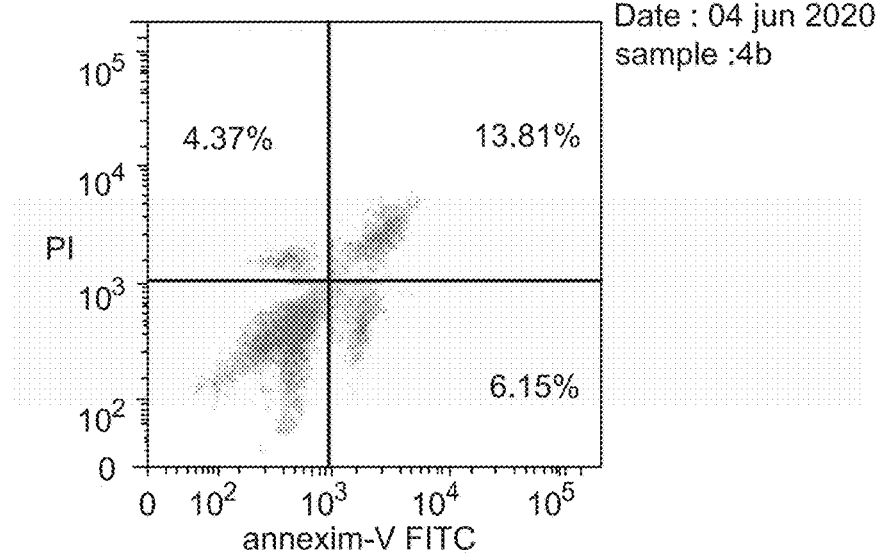

The molecular structures of compounds 4a to 4l, as obtained by the process described in FIG. 8, are provided in FIG. 9. The compounds are 2,7,7-trimethyl-5-oxo-4-(4-(phenylsulfonyl)phenyl)-1,4,5,6,7,8-hexahydroquinoline-3-carboxylate (4a); ethyl 7,7-dimethyl-5-oxo-4-(4-(phenylsulfonyl)phenyl)-2-(trifluoromethyl)-1,4,5,6,7,8-hexahydroquinoline-3-carboxylate (4b); ethyl 2-amino-7,7-dimethyl-5-oxo-4-(4-(phenylsulfonyl)phenyl)-1,4,5,6,7,8-hexahydroquinoline-3-carboxylate (4c); 2-amino-3-benzoyl-7,7-dimethyl-4-(4-(phenylsulfonyl)phenyl)-4,6,7,8-tetrahydroquinolin-5(1H)-one (4d); 2-amino-7,7-dimethyl-3-(4-methylbenzoyl)-4-(4-(phenylsulfonyl)phenyl)-4,6,7,8-tetrahydroquinolin-5(1H)-one (4e); 2-amino-3-(4-bromobenzoyl)-7,7-dimethyl-4-(4-(phenylsulfonyl) phenyl)-4,6,7,8-tetrahydroquinolin-5(1H)-one (4f); methyl 2,7,7-trimethyl-5-oxo-4-(4-tosylphenyl)-1,4,5, 6,7,8-hexahydroquinoline-3-carboxylate (4g); ethyl 7,7-dimethyl-5-oxo-4-(4-tosylphenyl)-2-(trifluoromethyl)-1,4,5,6,7,8-hexahydroquinoline-3-carboxylate (4h); ethyl 2-amino-7,7-dimethyl-5-oxo-4-(4-tosylphenyl)-1,4,5,6,7,8-hexahydroquinoline-3-carboxylate (4i); 2-amino-3-benzoyl-7,7-dimethyl-4-(4-tosylphenyl)-4,6,7,8-tetrahydroquinolin-5(1H)-one (4j); 2-amino-7,7-dimethyl-3-(4-methylbenzoyl)-4-(4-tosylphenyl)-4,6,7,8-tetrahydroquinolin-5(1H)-one (4k); and 2-amino-3-(4-bromobenzoyl)-7,7-dimethyl-4-(4-tosylphenyl)-4,6,7,8-tetrahydroquinolin-5(1H)-one (4l).

The tetrahydroquinoline-phenylsulfonyl derivatives obtained by the process of the present disclosure are obtained in a short reaction time with high yields, unlike conventional methods.

EXAMPLES

The disclosure will now be illustrated with examples, which are intended to illustrate the working of disclosure and not intended to take restrictively to imply any limitations on the scope of the present disclosure.

Materials and Methods

All melting points were measured on a Gallenkamp Electrothermal melting points apparatus and was uncorrected. The Infrared spectra (KBr disks) in the range of 4000 to 400 cm$^{-1}$ was recorded on Perkin-Elmer Frontier spectrometer (USA). The second IR device is Spectrum two FT-IR Spectrometer, detector type LiTaO$_3$, wavelength range 8300-350 cm$^{-1}$. The NMR spectra were recorded on 850 and 600 MHz NMR spectrometer deuterated in dimethylsulphoxide (DMSO-d$_6$) and deureated chloroform (CDCl$_3$). Chemical shifts are quoted in δ and were related to that of the solvent. Mass spectrum was carried out on direct probe controller inlet part to single quadropole mass analyzer in (Thermo Scientific GCMS) (Model (ISQ LT) using Thermo X-Calibur Software at the regonal center for mycology and biotechnology (RCMB) Al-Azhar University, NASER city, Cairo. X-ray crystallography was carried out on Kappa CCD Enraf Nonius FR 590 diffractometer, Kuwait. Ultrasound irradiation was carried out with a microprocessor controlled-2004, high intensity ultrasonic processor with temperature controller (750 W). The ultrasonic frequency of the cleaning bath used was equal to 25 KHz. The reaction temperature was manual input depended on boiling point of solvent used and stabilized even more than hour. Q-tube assisted reactions were performed in Q-tube safe pressure reactor from Q Labtech, equipped with a cap/sleeve, pressure adapter (120 psi), needle, borosilicate glass tube, Teflon septum and catch bottle. Elemental analyses were performed using Perkin-Elmer 2400 Analyser. TLC Sigma-Aldrich, Silica gel on TLC Al foils, silica gel matrix, with fluorescent indicator 254 nm.

Example 1: General process for the preparation of 4,6,7,8-tetrahydroquinolin-5(1H)-one derivatives under conventional conditions A mixture of dimedone (1) (1 mmol), different aldehydes 2a, b (1 mmol), active methylene compounds 3a-f (1 mmol) and ammonium acetate (9 mmol) in ethanol (25 ml) containing a catalytic amount of Cu-chitosan NPs (0.1 g) was refluxed at 60° C. for 5 hours (as can be observed below in Table 1) until completion of the reaction (monitored by TLC). The reaction mixture was filtered to separate the catalyst; then, the filtrate was cooled at room temperature, and the reliable product obtained was filtered, dried, and purified by recrystallisation from ethanol.

Example 2: General process for the preparation of 4,6,7,8-tetrahydroquinolin-5(1H)-one derivatives under ultrasound conditions These processes were performed on the same scale described above for silent reactions. All the reactions were kept at 60° C., which was attained by adding or removing water in an ultrasonic bath (the temperature inside the reaction vessel was 58-63° C.). The sonochemical reactions were continued for a suitable time (as can be observed below in Table 1) until the starting materials were no longer detectable by TLC. The catalyst was further separated, and the products obtained were purified by recrystallisation from ethanol in silent reaction procedures. The synthesized compounds with their physical data are provided in Table 1.

TABLE 1

| S.No | Compound | Conventional conditions | | Ultrasound conditions | |
|---|---|---|---|---|---|
| | | Time (h) | Yield (%) | Time (minutes) | Yield (%) |
| 4a | 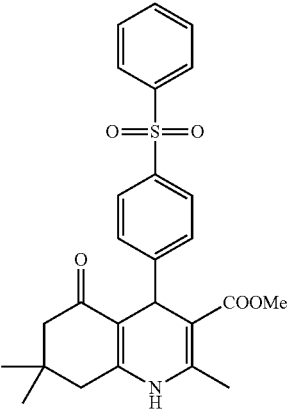 | 5 | 80 | 20 | 93 |

TABLE 1-continued

| | | Conventional conditions | | Ultrasound conditions | |
|---|---|---|---|---|---|
| S.No | Compound | Time (h) | Yield (%) | Time (minutes) | Yield (%) |
| 4b | ![structure] | 5 | 78 | 20 | 92 |
| '4c | ![structure] | 6 | 84 | 25 | 95 |
| 4d | ![structure] | 6 | 80 | 30 | 92 |

TABLE 1-continued

| S.No | Compound | Conventional conditions | | Ultrasound conditions | |
|---|---|---|---|---|---|
| | | Time (h) | Yield (%) | Time (minutes) | Yield (%) |
| 4e | | 6 | 78 | 30 | 90 |
| 4f | | 6 | 78 | 30 | 90 |
| 4g | | 5 | 84 | 25 | 95 |

TABLE 1-continued

| S.No | Compound | Conventional conditions | | Ultrasound conditions | |
|------|----------|------|------|------|------|
| | | Time (h) | Yield (%) | Time (minutes) | Yield (%) |
| 4h | | 5 | 82 | 25 | 95 |
| 4i | | 5 | 84 | 25 | 93 |
| 4j | | 6 | 79 | 30 | 92 |

TABLE 1-continued

| S.No | Compound | Conventional conditions | | Ultrasound conditions | |
|------|----------|------------|-----------|---------------|-----------|
|      |          | Time (h)   | Yield (%) | Time (minutes)| Yield (%) |
| 4k   | *[structure: 7,7-dimethyl-4-(4-(p-tolylsulfonyl)phenyl)-3-(4-methylbenzoyl)-2-amino-4,6,7,8-tetrahydroquinolin-5(1H)-one]* | 6 | 78 | 30 | 92 |
| 4l   | *[structure: 7,7-dimethyl-4-(4-(p-tolylsulfonyl)phenyl)-3-(4-bromobenzoyl)-2-amino-4,6,7,8-tetrahydroquinolin-5(1H)-one]* | 6 | 78 | 30 | 90 |

The beneficial effect of ultrasound irradiation (sonication) is noticeable over conventional conditions on this reaction (Table 1), reducing the reaction time from 5 to 6 h into 20-30 minutes. Also, an increase in yield to 90-95% was observed under ultrasound irradiation compared to 78-84% under conventional conditions. The apparent effect of ultrasound on the reaction may be attributed to the fact that ultrasonic irradiation gives the reactants sufficient energy to exceed the energy barrier of the reaction. The reaction products were identified as the polysubstituted 4,6,7,8-tetrahydroquinolin-5(1H)-ones 4a-4l in all cases based on its $^1$H NMR spectrum and $^{13}$C NMR spectra. The spectral data for all the compounds is presented in the subsequent examples.

Example 3: Methyl 2,7,7-trimethyl-5-oxo-4-(4-(phenylsulfonyl)phenyl)-1,4,5,6,7,8-hexahydroquinoline-3-carboxylate (4a). Melting point: 260-262° C. (4a)

IR (KBr) $v_{max}$/cm$^{-1}$: 3213 (NH), 1714, 1688 (2 C=O), 1310, 1211 (SO$_2$); 1H NMR (400 MHz, DMSO-d$_6$): δ 0.80 (s, 3H, CH$_3$), 0.98 (s, 3H,CH$_3$), 1.97 (d, 1H, J$^1$/$_4$16 Hz, H-8a), 2.15 (d, 1H, J=16 Hz, H-8b), 2.28 (s, 3H, CH3), 2.33 (d, 1H, J=16.4 Hz, H-6a), 2.41 (d, 1H, J=16.4 Hz, H-6b), 3.49 (s, 3H, CH$_3$ ester), 4.91 (s, 1H, CH-4), 7.35 (d, 2H, J=7.6 Hz, ArH), 7.39 (d, 2H, J=7.72 Hz, ArH), 7.76-7.80 (m,5H, ArH), 9.21 (br's, 1H, NH, D$_2$O exchangeable). $^{13}$C NMR (100 MHz, DMSO-δ6): d 18.8, 27.1, 29.3, 32.7, 36.7, 50.5, 51.3, 102.7, 109.6, 127.5, 127.8, 132.1, 138.9, 144.7, 153.4, 167.4, 194.8; MS m/z (%): 465 (M$^+$, 40.9). Anal. for C$_{26}$H$_{27}$NO$_5$S: C, 67.08; H, 5.85; N, 3.01; S, 6.89. found: C, 67.29; H, 5.79; N, 2.90; S, 6.83%.

Example 4: Ethyl 7,7-dimethyl-5-oxo-4-(4-(phenylsulfonyl)phenyl)-2 (trifluoromethyl)-1,4,5,6,7,8-hexahydroquinoline-3-carboxylate (4b)

Melting point: 245-247° C. IR (KBr) $v_{max}$/cm$^{-1}$: 3221 (NH), 1717, 1688 (2 C$^1$/$_4$O), 1314, 1210 (SO$_2$); $^1$H NMR (400 MHz, DMSO-d$_6$): δ 0.85 (s,3H, CH$_3$), 0.98 (s, 3H, CH$_3$), 1.13 (t, 3H, J=7Hz CH$_3$ ester) 1.96 (d,1H, J=16 Hz, H-8a), 2.16 (d, 1H, J=16 Hz, H-8b), 2.35 (d, 1H, J=16.4 Hz, H-6a), 2.43 (d, 1H, J=16.4 Hz, H-6a), 4.19 (q, 2H,J=7 Hz, CH$_2$ ester), 4.92 (s, 1H, CH-4), 7.35 (δ, 2H, J=7.6 Hz, ArH), 7.39 (δ, 2H, J=7.72 Hz, ArH), 7.71-7.86 (m, 5H, ArH), 9.22 (br's, 1H,NH, D$_2$O exchangeable). $^{13}$C NMR (100 MHz, DMSO-δ6): d 18.9, 27.1, 29.3, 32.7, 36.7, 51.3, 62.0, 102.6, 109.5, 123.2, 127.6, 127.7, 130.2, 134.9, 138.9, 141.7, 146.7, 150.6, 153.6, 167.4, 194.7; MS m/z (%): 533 (M+: 51.5). Anal. for $C_{27}F_3NO_5S$: C, 60.78; H, 4.91; N; 2.63; S, 6.01. found: C, 60.99; H, 4.87; N, 2.53; S, 5.94%.

Example 5: Ethyl 2-amino-7,7-dimethyl-5-oxo-4-(4-(phenylsulfonyl)phenyl)-1,4,5,6,7,8-hexahydroquinoline-3-carboxylate (4c).

Melting point: 238-240° C. IR (KBr) $v_{max}/cm^{-1}$: 3389, 3282 (NH$_2$), 3216 (NH), 1712, 1689 (2C=O), 1310, 1196 (SO$_2$); $^1$H NMR (400 MHz, CDCl$_3$): δ 0.96 (s, 3H, CH$_3$), 1.09 (s, 3H, CH$_3$), 1.14(t, 3H, J=7.2 Hz, CH$_3$ ester), 1.84 (br's, 2H, NH$_2$, D$_2$O exchangeable), 2.17 (dd, 2H, J=14 Hz, H-8a and H8b), 2.41 (s, 2H, CH$_2$-6), 4.03(q, 2H, J=7.2 Hz, CH$_2$ ester), 4.66 (s, 1H, C4-H), 7.15 (δ, 2H, J=7.6 Hz, ArH), 7.21 (δ, 2H, J=7.72 Hz, ArH), 7.39-7.78 (m,5H, ArH), 9.54 (br's, 1H, NH, D$_2$O exchangeable). $^{13}$C NMR (100 MHz, CDCl$_3$): δ 14.2, 27.4, 29.1, 32.2, 33.5, 40.7, 50.7, 59.8, 80.3, 116.4, 122.0, 126.9, 127.9, 129.6, 131.6, 136.0, 144.5, 149.5, 158.4, 161.5, 168.9, 196.4; MS m/z (%): 480 (M$_+$, 28.7). Anal. for $C_{26}H_{28}N_2O_5S$: C, 64.98; H, 5.87; N, 5.83; S, 6.67. found: C, 65.20; H, 5.81; N, 5.75; S, 6.59%.

Example 6: 2-Amino-3-benzoyl-7,7-dimethyl-4-(4-(phenylsulfonyl)phenyl)-4,6,7,8-tetrahydroquinolin-5(1H)-one (4d).

Melting point: 300° C. IR (KBr) $v_{max}/cm^{-1}$: 3339, 3291 (NH$_2$), 3222 (NH), 1699, 1685 (2 C=O), 1310, 1206 (SO$_2$); $^1$H NMR (850 MHz, CDCl$_3$): δ 0.96 (s, 3H, CH$_3$), 1.09 (s, 3H, CH$_3$), 2.18 (dd, 2H, J=14 Hz, H-8a and H-8b), 2.42 (dd, 2H, J=16.9 Hz, H-6a and H-6b), 4.65 (s, 1H, CH-4), 6.21 (br's, 2H,NH$_2$, D$_2$O exchangeable), 6.82 (d, 2H, J=7.4 Hz, ArH), 7.14 (d, 2H, J=7.6 Hz, ArH), 7.33 (d, 2H, J=7.1 Hz, ArH), 7.56-7.81 (m, 4H, ArH), 8.11-8.48 (m, 4 h, ArH), 9.31 (br's, 1H, NH, D$_2$O exchangeable). $^{13}$C NMR (213 MHz, CDCl3): d 27.3, 29.1, 32.3, 33.4, 40.6, 50.7, 80.2, 50.5, 51.3, 116.3, 126.2, 127.4, 128.1, 129.7, 129.9, 130.1, 130.8, 134.2, 137.3, 144.9, 145.1, 158.3, 168.9, 190.7, 196.5; MS m/z (%): 512 (M+, 39.1). Anal. for $C_{30}H_{28}N_2O_4S$: C, 70.29; H, 5.51; N, 5.46; S, 6.25. found: C, 70.52; H, 5.47; N, 5.36; S, 6.17%.

Example 7: 2-Amino-7,7-dimethyl-3-(4-methylbenzoyl)-4-(4-(phenylsulfonyl) phenyl)-4,6,7,8-tetrahydroquinolin-5(1H)-one (4e).

Melting point: 300° C. IR (KBr) $v_{max}/cm^{-1}$: 3331, 3291 (NH$_2$), 3226 (NH), 1691, 1683 (2 C=O), 1314, 1201(SO$_2$); $^1$H NMR (850 MHz, CDCl3): δ 0.96 (s, 3H, CH3), 1.09 (s, 3H, CH$_3$), 2.17 (dd, 2H, J=16.15 Hz, H-8a and H-8b), 2.41 (dd, 2H, J=17.83 Hz, H-6a and H-6b), 2.58 (s, 3H, CH3), 4.69 (s, 1H, C4-H), 6.26 (br's, 2H, NH2, D2O exchangeable), 6.87 (d,2H, J=8.5 Hz), 6.88-6.89 (m, 5H, ArH), 7.20-7.23 (m, 4H, ArH), 7.27 (d, 2H, J=8.4 Hz, ArH), 9.05 (br's, 1H, NH, D2O exchangeable). $^{13}$C NMR (213 MHz, CDCl3): δ 18.2, 27.3, 29.1, 32.2, 33.2, 40.6, 50.7, 80.5, 116.6, 128.8, 129.6, 129.9, 131.2, 133.6, 137.4, 139.2, 141.6, 158.3, 169.0, 189.9, 196.5; MS m/z (%): 526 (Mp, 74.3). Anal. For C31H30N2O4S: C, 70.70; H, 5.74; N, 5.32; S, 6.09. found: C, 70.88; H, 5.71; N, 5.24; S, 6.04%.

Example 8: 2-Amino-3-(4-bromobenzoyl)-7,7-dimethyl-4-(4-(phenylsulfonyl) phenyl)-4,6,7,8-tetrahydroquinolin-5(1H)-one (4f).

Melting point: 300° C. IR (KBr) $v_{max}/cm^{-1}$: 3310, 3296 (NH$_2$), 3221 (NH), 1691, 1682 (2C=O), 1305, 1193 (SO$_2$); $^1$H NMR (850 MHz, DMSO-d$_6$): δ 0.96 (s, 3H, CH3), 1.04 (s, 3H, CH$_3$), 2.13 (dd, 2H, J=16.00 Hz, H-8a and H-8b), 2.42 (dd, 2H, J=16.4 Hz, H-6a and H-6b), 4.62 (s, 1H,C4-H), 6.23 (br's, 2H, NH$_2$, D$_2$O exchangeable), 6.91-7.16 (m, 7H, ArH), 7.33-7.52 (m, 4H, Ar H), 7.65 (d, 2H, J=8.2 Hz, ArH), 9.11 (br's, 1H, NH, D$_2$O exchangeable). $^{13}$C NMR (213 MHz, CDCl$_3$): δ 27.3, 29.1, 32.2, 33.2, 40.6, 50.7, 80.5, 116.6, 128.8, 129.6, 129.9, 131.2, 133.6, 137.4, 139.2, 141.6, 158.3, 169.0, 189.9, 196.5; MS m/z (%): 591 (M+, 77.1), 593 (M+2, 76.8). Anal. for $C_{30}H_{27}BrN_2O_4S$: C, 60.92; H, 4.60; N, 4.74; S, 5.42. found: C, 61.11; H, 4.55; N, 4.65; S, 5.37%.

Example 9: Methyl 2,7,7-trimethyl-5-oxo-4-(4-tosylphenyl)-1,4,5,6,7,8-hexahydroquinoline-3-carboxylate (4g).

Melting point: 236-238° C. IR (KBr) $v_{max}/cm^{-1}$:3218 (NH), 1723, 1674 (2 C=O), 1312, 1206 (SO$_2$); $^1$H NMR (850 MHz, CDCl$_3$): δ 0.91 (s, 3H, CH$_3$), 1.01 (s, 3H, CH$_3$), 2.02 (d, 1H, J=16 Hz, H-8a), 2.09 (d, 1H, J=16 Hz, H-8b), 2.33 (s, 3H,CH$_3$), 2.34 (s, 3H, CH$_3$), 2.36 (s, 2H, CH$_2$-6), 4.42 (s, 1H, C4-H), 3.16 (s, 3H, CH$_3$ ester), 4.41 (s, 1H, CH-4), 6.70 (d, 2H, J=7.6 Hz, ArH), 6.87 (d, 2H, J=7.8 Hz, ArH), 7.56-7.81 (m, 4H, ArH), 9.12 (br's, 1H, NH, D$_2$O exchangeable). $^{13}$C NMR (213 MHz, CDCl$_3$): d 19.2, 21.3, 27.3, 28.3, 32.2, 39.5, 40.8, 49.7, 50.2, 104.2, 117.6, 128.8, 129.4, 134.1, 136.1, 153.6, 154.2, 156.1, 164.3, 197.6; MS m/z (%): 479; (M$_+$, 49), Anal. for $C_{27}H_{29}NO_5S$: C, 67.62; H, 6.10; N, 2.92; S, 6.68.found: C, 67.80; H, 6.06; N, 2.83; S, 6.63%.

Example 10: Ethyl 7,7-dimethyl-5-oxo-4-(4-tosylphenyl)-2-(trifluoromethyl)-1,4,5,6,7,8-hexahydroquinoline-3-carboxylate (4h).

Melting point: 241-243° C. IR (KBr) $v_{max}/cm^{-1}$: 3231 (NH), 1726, 1684 (2 C=O), 1303, 1215 (SO$_2$); $^1$H NMR (400 MHz, DMSO-d6): δ 0.89 (s, 3H, CH$_3$), 1.01 (s, 3H, CH$_3$), 1.16 (t, 3H, J=7 Hz CH$_3$ ester), 2.01 (d, 1H, J=16 Hz, H-8a), 2.14 (d, 1H, J=16 Hz, H-8b), 2.33 (d, 1H, J=16.4 Hz, H-6a), 2.43 (d, 1H, J=16.4 Hz, H-6b), 2.48 (s, 3H, CH$_3$), 4.12 (q, 2H, J=7 Hz, CH$_2$ ester), 4.91 (s, 1H, CH-4), 7.31 (d, 2H, J=7.00 Hz, ArH), 7.41-7.56 (m, 4H, ArH), 7.58 (d, 2H, J=7.72 Hz, ArH), 9.26 (br's, 1H, NH, D$_2$O exchangeable). $^{13}$C NMR (100 MHz, DMSO-d$_6$): δ 14.3, 18.2, 27.3, 29.1, 32.5, 37.2, 43.6, 51.1, 62.0, 100.4, 113.5, 124.2, 128.6, 129.2, 129.8, 130.2, 136.7, 138.2, 141.8, 146.7, 150.6, 153.6, 168.6, 194.8; MS m/z (%): 547 (M+, 39), Anal. For $C_{28}H_{28}F_3NO_5S$: C, 61.42; H, 5.15; N, 2.56; S, 5.85. found: C, 61.63; H, 5.09; N, 2.46; S, 5.79%.

Example 11: Ethyl 2-amino-7,7-dimethyl-5-oxo-4-(4-tosylphenyl)-1,4,5, 6,7,8-hexahydroquinoline-3-carboxylate (4i).

Melting point: 281-283° C. IR (KBr) $v_{max}/cm^{-1}$: 3394, 3286 (NH$_2$), 3231(NH), 1726, 1684 (2C=O), 1303, 1215 (SO$_2$); 1H NMR (400 MHz, DMSO-d$_6$): δ 0.92 (s, 3H, CH$_3$), 0.99 (s, 3H, CH$_3$), 1.12(t, 3H, J=7.2 Hz, CH$_3$ ester), 1.89 (br's, 2H, NH$_2$, D$_2$O exchangeable), 2.11 (dd, 2H, J=14 Hz, H-8a and H8b), 2.36 (s, 2H, CH2-6), 2.44 (s, 3H, CH$_3$), 4.11(q, 2H, J=7.2 Hz, CH$_2$ ester), 4.71 (s, 1H, C4-H), 7.15 (d, 2H, J=7.2 Hz, ArH), 7.21 (d, 2H, J=7.6 Hz, ArH), 7.36-7.52 (m, 5H, ArH), 9.21 (br's, 1H, NH, D$_2$O exchangeable). $^{13}$C NMR (100 MHz, CDCl$_3$): δ 14.3, 18.9, 27.3, 29.6, 32.4, 35.2, 41.7, 52.4, 59.6, 83.1, 117.7, 127.6, 127.7, 129.7, 130.6, 133.9, 136.3, 138.3, 145.5, 149.5, 161.9, 168.7, 194.5; MS m/z (%): 494 (M⁺, 62.9), Anal. for $C_{27}H_{30}N_2O_5S$: C, 65.57; H, 6.11; N, 5.66; S, 6.48. found: C, 65.74; H, 6.06; N, 2.39; S, 6.41%.

Example 12: 2-Amino-3-benzoyl-7,7-dimethyl-4-(4-tosylphenyl)-4,6,7,8 tetrahydroquinolin-5(1H)-one (4j).

Melting point: 300° C. IR (KBr) $v_{max}$/cm⁻¹: 3382, 3267 (NH₂), 3211(NH), 1691, 1681 (2 C=O), 1310, 1211 (SO₂); ¹H NMR (850 MHz, CDCl₃): δ 0.94 (s, 3H, CH₃), 1.01 (s, 3H, CH₃), 2.22 (dd, 2H, J=14 Hz, H-8a and H-8b), 2.31 (dd, 2H, J=16.9 Hz, H-6a and H-6b), 2.38 (s, 3H, CH₃), 4.52 (s, 1H, CH-4), 6.28 (br's, 2H, NH₂, D₂O exchangeable), 6.79 (d, 2H, J=7.8 Hz, ArH), 7.32 (d, 2H, J=7.4 Hz, ArH), 7.46-7.71 (m, 4H, ArH), 7.77-8.01(m, 4H, ArH), 9.31 (br's, 1H, NH, D₂O exchangeable). ¹³C NMR (213 MHz, CDCl3): δ 18.23, 27.3, 29.2, 32.4, 34.2, 40.8, 50.1, 81.3, 50.5, 51.3, 116.3, 126.2, 127.4, 128.1, 129.7, 129.9, 130.1, 130.8, 134.2, 137.3, 144.9, 145.1, 158.3, 168.9, 190.7, 196.5; MS m/z (%): 526 (M⁺, 41.3), Anal. for $C_{31}H_{30}N_2O_4S$: C, 70.70; H, 5.74; N, 5.32; S, 6.09. found: C, 70.87; H, 5.69; N, 5.25; S, 6.02%.

Example 13: 2-Amino-7,7-dimethyl-3-(4-methylbenzoyl)-4-(4-tosylphen yl)-4,6,7,8-tetrahydroquinolin-5(1H)-one (4k).

Melting point: 300° C. IR (KBr) $v_{max}$/cm⁻¹: 3379, 3229 (NH₂), 3211(NH), 1690, 1676 (2 C=O), 1310, 1196 (SO₂); ¹H NMR (850 MHz, CDCl₃): δ 0.93 (s, 3H, CH₃), 0.97 (s,3H, CH₃), 2.01 (dd, 2H, J=16 Hz, H-8a and H-8b), 2.22 (dd, 2H, J=16.2 Hz, H-6a and H-6b), 2.36 (s, 3H, CH₃), 2.39 (s, 3H, CH₃), 4.61 (s, 1H, C4-H), 6.01 (br's, 2H, NH₂, D₂O exchangeable), 7.22-7.41 (m, 4H, ArH), 7.49(d, 2H, J=7.2 Hz, ArH), 7.56-7.67 (m, 4H, ArH), 7.77 (d, 2H, J=7.8 Hz, ArH), 9.23 (br's, 1H, NH, D₂O exchangeable). ¹³C NMR (213 MHz, CDCl₃): δ 18.7, 19.1, 27.2, 29.4, 32.8, 37.1, 39.9, 51.1, 80.3, 116.5, 128.5, 128.8, 129.5, 129.7, 130.3, 130.9, 132.1, 138.3, 138.9, 139.0, 144.1, 152.5, 156.1, 168.9, 189.2, 195.6; MS m/z (%): 540 (M⁺, 65.1), Anal. for $C_{32}H_{32}N_2O_4S$: C, 71.09; H, 5.97; N, 5.18; S, 5.93. found: C, 71.29; H, 5.93; N, 5.08; S, 5.87%.

Example 14: 2-Amino-3-(4-bromobenzoyl)-7,7-dimethyl-4-(4-tosylphenyl)-4,6,7,8-tetrahydroquinolin-5(1H)-one (4l).

Melting point>300° C. IR (KBr) $v_{max}$/cm⁻¹: 3379, 3229 (NH₂), 3211(NH), 1690, 1676 (2 C=O), 1310, 1196 (SO₂); ¹H NMR (850 MHz, DMSO-d₆): δ 0.93 (s, 3H, CH₃), 1.01 (s, 3H, CH₃), 2.11 (dd, 2H, J=16.00 Hz, H-8a and H-8b), 2.31 (dd, 2H, J=16.4 Hz, H-6a and H-6b), 2.39 (S, 3H, CH₃), 4.45 (s, 1H, C4-H), 6.41 (br's, 2H, NH₂, D₂O exchangeable), 7.21-7.46 (m, 8H, ArH), 7.53-7.74 (m, 2H, ArH), 7.85 (d, 2H, J=7.8 Hz, ArH), 9.29 (br's, 1H, NH, D₂O exchangeable). ¹³C NMR (213 MHz, CDCl₃): δ 19.2, 27.1, 29.6, 32.4, 36.2, 40.1, 50.7, 80.9, 115.1, 127.9, 128.3, 129.8, 129.9, 131.6, 133.4, 138.6, 140.0, 148.6, 151.1, 168.4, 190.3,196.8; MS m/z (%): 605 (M₊, 29.6), 607 (M₊₂, 29.5). Anal. for $C_{31}H_{29}BrN_2O_4S$: C, 61.49; H, 4.83; N, 4.63; S, 5.29. found: C, 61.68; H, 4.79; N, 4.55; S, 5.25%.

Experimental Section

Biological activity: In vitro anticancer screening

A series of compounds bearing 7,7-dimethyl-4-(4-(phenylsulfonyl) phenyl)-4,6,7,8-tetrahydroquinolin-5(1H)-one scaffold, as observed in Table 1, were evaluated for their potential anti-breast cancer activity. In order to evaluate the cytotoxic activity of the compound represented by Formula (II), it was subjected to 3-(4,5-dimethylthiazol-2-yl)-2,5-diphenyl tetrazolium bromide (MTT) cell viability assay against human breast cancer MCF-7 cell line using staurosporine as a reference drug. For this purpose, cells suspended in the medium (2×10⁴ cells/mL) were plated in 96-well culture plates and incubated at 37° C. in a 5% CO₂ incubator. After 12 h, the test sample (2 pL) was added to the cells (2×10⁴) in 96-well plates and cultured at 37° C. for 3 days. The cultured cells were mixed with 20 μL (microlitre) of MTT solution and incubated for 4 h at 37° C. The supernatant was carefully removed from each well and 100 pL of DMSO were added to each well to dissolve the formazan crystals which were formed by the cellular reduction of MTT. After mixing with a mechanical plate mixer, the absorbance of each well was measured by a microplate reader using a test wavelength of 570 nm (nanometers). The results were expressed as the IC₅₀ (micromolar or μM) value, which represents inducing a 50% inhibition of cell growth of the treated cells when compared to the growth of control cells. Each experiment was performed at least 3 times. There was a good reproducibility between the replicate wells with standard errors. The results of this study are tabulated in Table 2.

TABLE 2

In vitro cell cytotoxic activity of the compound 4 against MCF-7 cancer cells

| Compound No | Anticancer activity against MCF-7 cells IC₅₀ (μM) |
|---|---|
| 4a | 0.103 ± 0.013 |
| 4b | 0.002 ± 0.001 |
| 4c | 0.015 ± 0.002 |
| 4d | 0.007 ± 0.001 |
| 4e | 0.004 ± 0.002 |
| 4f | 0.027 ± 0.014 |
| 4g | 0.027 ± 0.003 |
| 4h | 0.041 ± 0.006 |
| 4i | 0.023 ± 0.003 |
| 4j (compound of Formula (II)) | 0.003 ± 0.005 |
| 4k | 0.004 ± 0.001 |
| 4l | 0.007 ± 0.001 |
| Staurosporine | 0.005 ± 0.0007 |

From the Table 2 it can be observed that the derivatives showed variable degrees of cytotoxic activities. 2-trifluoromethyl derivative, 4b, exhibited about 2.5-fold more potent activity than the standard drug staurosporine (IC₅₀ of 4b was found to be 0.002 mM, and IC₅₀ staurosporine; 0.005 mM). The potent cytotoxic effect of 4b could be explained due to the electron withdrawing power of fluorine atom, alongside the increased carbon-fluorine bond energy, that significantly potentiates the metabolic stability of the host molecule and enhance its lipophilicity, thereby facilitating the cell membrane permeation and its pronounced cytotoxic effect. A slight decrease in the potency was detected upon replacement of -CF₃ group by NH₂ as compounds 4j, 4e, 4k exhibiting about 1-1.6-fold more potent activity than that resulted by staurosporine. The IC₅₀ values of 4j, 4e, 4k are 0.003, 0.004, and 0.004 mM, respectively. Further decrease in the inhibitory activity to be 1.4-fold less potent than the standard drug was obtained upon replacement of the 3-methoxy/ethoxy groups by phenyl or p-bromophenyl groups as compounds 4d, and 4l exhibited an IC₅₀ 0.007 mM. The rest of the compounds produced a detectable decrease in the cytotoxic potency of $IC_{50}$ ranging from 0.023 to 0.103 mM. The effect of compound 4j against normal WI38 cells One of the features that differentiates various antiproliferative therapeutic agents from each other is the recurrence and severity of their side effects to the normal cells at their therapeutic doses. Accordingly, the safety profile of the most promising candidates (4b, 4j, 4k, and 4e) was evaluated against the normal WI38 cells derived from lung tissues using MTT assay. The results were compared with the reference drug Staurosporine. The results of this study are presented in Table 3.

TABLE 3

The effect of some compounds as representative examples against the normal WI38 cells

| Compound No. | IC50 (µM) |
|---|---|
| 4e | 0.0149 ± 0.003 |
| 4j | 0.048 ± 0.008 |
| 4b | 0.045 ± 0.013 |
| 4k | 0.0176 ± 0.009 |
| Staurosporine | 0.013 ± 0.002 |

From Table 3, it can be observed that the $IC_{50}$ values of the target compounds 4j, 4b against the normal WI38 cells were 20 and 24-fold higher than their $IC_{50}$ doses against the cancer cells and about 3-fold higher than the $IC_{50}$ value of reference drug staurosporine, confirming a promising safety profile of both compounds. The safety profile was found to be lesser with compounds 4e and 4k producing $IC_{50}$ values against WI38 cells that were only 4-fold higher than their $IC_{50}$ doses against MCF-7 cells and approximately equal to that obtained by staurosporine.

In vitro kinase inhibition assay

RTK's play essential roles in regulation of cell proliferation, differentiation, survival and apoptosis. Aberrant expression of RTK results in cell growth dysfunction leading to tumor takeover, angiogenesis, and metastasis. They also produce their actions in a synergistic pattern in regulating tumor response to different anticancer RTK inhibitor drug therapies. Accordingly, RTKs are considered as successful molecular targets for various anticancer therapies, specifically for advancing new multi-target anticancer drugs of improved therapeutic efficacies. To explore the mechanistic insight into the cytotoxic potentials of the compounds as provided in Table 1, an in vitro kinase assay was performed to evaluate the kinase suppression activity of the most promising cytotoxic candidates 4b, 4j against four different receptor tyrosine kinases (RTKs) - namely epidermal growth factor receptor (EGFR), human epidermal growth factor receptor (HER2), vascular endothelial growth factor receptor-2 (VEGFR-2) and platelet-derived growth factor receptor (PDGFR). The activities of the examined compounds against EGFR, HER2, PDGFR-β, and VEGFR2 were in vitro tested using Abcam's Human In cell ELISA Kit (ab 126419) for EGFR, ADP-Glo TM Kinase Assay for Her2, PDGFR-β, active, recombinant protein expressed in Sf9 cells for VEGFR2 (KDR) Kinase Assay Kit Catalog #40325, respectively. The procedure of the used kits was done according to the manufacturer's instructions. The results of this study are presented in Table 4.

TABLE 4

Protein kinase inhibition of compounds 4b and 4j in comparison with Sorafenib

| Compound No | EGFR $IC_{50}$ ng/ml | HER-2 $IC_{50}$ ng/ml | PDGFR-β $IC_{50}$ ng/ml | VEGFR-2 $IC_{50}$ ng/ml |
|---|---|---|---|---|
| 4b | 0.11 ± 0.03 | 0.30 ± 0.05 | 0.21 ± 0.04 | 1.05 ± 0.02 |
| 4j | 0.07 ± 0.02 | 0.17 ± 0.02 | 0.07 ± 0.01 | 0.30 ± 0.06 |
| Sorafenib | 0.04 ± 0.02 | 0.28 ± 0.04 | 0.13 ± 0.02 | 0.17 ± 0.02 |

It has been detected that compound 4j was more potent than 4b as EGFR inhibitor with $IC_{50}$ values of $0.07 \times 10^{-3}$ and $0.11 \times 10^{-3}$ mM, respectively, but both were less potent than the Sorafenib, whose $IC_{50}$ value was $0.04 \times 10^{-3}$ mM. On the other hand, compound 4j exhibited a significant inhibitory effect against HER-2, which is about 1.6 folds more potent than the Sorafenib. The $IC_{50}$ value for compound 4j was found to be $0.17 \times 10^{-3}$ mM, and $IC_{50}$ Sorafenib was $0.28 \times 10^{-3}$ mM. Also, compound 4j notably inhibited PDGFR-a by 1.9-fold more than the reference sorafenib of $IC_{50}$. Furthermore, both compounds 4b and 4j revealed VEGFR-2 inhibitory effect of about 6.2 and 1.8-fold less than that of Sorafenib. The obtained data revealed the distinct inhibitory profile of the amino tetrahydroquinoline derivative 4j in comparison with the reference drug sorafenib as illustrated in Table 3.

From the Table 3, it can be observed that the compound 4j has a potency as EGFR inhibitors with $IC_{50}$ values of 40.74 ng/ml (nanogram per milliliter), respectively when compared with sorafenib (reference drug) of $IC_{50}$ 23.92 ng/ml. In addition, compound 4j exhibited significant inhibitory effect on HER-2 ($IC_{50}$ 90.2 ng/ml)-about 1.5-fold more potent than sorafenib ($IC_{50}$ sorafenib=138 ng/ml). Also, compound 4j notably inhibited PDGFR-β by 0.7-fold more than the reference sorafenib of $IC_{50}$; 43 ng/ml, 60 ng/ml, respectively. Furthermore, compound 4j revealed VEGFR-2 inhibitory effect ($IC_{50}$ value 160 ng/ml) 1.8 folds less than that of sorafenib ($IC_{50}$ sorafenib; 88 ng/ml). The inhibitory effects of compound 4j in comparison with sorafenib against different RTK suggest that the compound 4j has a distinct inhibitory profile.

Apoptosis assay

The derivatives 4b and 4j were selected to study their apoptotic effects on MCF-7 cancer cells using Annexin-V/PI binding assay based on their promising cytotoxic potency and various kinase inhibitory effects. Staining MCF-7 cells was carried out with the two dyes; Annexin V/propidium iodide (PI) after treating them with compounds 4b and 4j at their $IC_{50}$ concentrations of 0.002 and 0.003 mM for 24 h. Flow cytometry method has been used to detect the corresponding red (PI) and green (FITC) fluorescence.

It has been observed that there was an increment in the percentages of the late apoptosis produced by the evaluated compounds 4b and 4j from 0.13% (control DMSO/MCF-7 cells) to 13.81% and 22.03%, respectively. Also, the tested compounds produced early apoptotic effects of 6.15% and 3.27% compared to 0.58% of the untreated MCF-7 cell with necrosis percent of 4.37% and 9.22%, respectively, vs. 0.66% produced by the DMSO control (FIGS. 10A-10C, FIGS. 11A-11C, and FIG. 12). The proportion of the late apoptosis produced by both 4b and 4j was higher than the proportion of the early phase, which makes recovering the dead cells to safe ones is more challenging. Cell cycle analysis The induction of apoptosis is one of the most crucial tools that confirm the effectiveness of cancer therapy. Cell cycle checkpoints are G1 (restriction or start), S (metaphase), and G2/M. One of the main functions of the anticancer therapeutics is stoppage of the cell division at these checkpoints. Thus, MCF-7 cells were incubated with compounds 4b and 4j at their $IC_{50}$ concentrations (0.002, 0.003 mM) for 24 h. The cells were stained with Annexin V/PI and examined using flow cytometry procedure. For cell cycle analysis, cell pellets were fixed with 70% ethanol on ice for 15 min. and collected again. The collected pellets were incubated with propidium iodide (PI) staining solution (50 mg/mL PI, 0.1 mg/mL RNaseA, 0.05% Triton X-100) at room temperature for 1 hand analyzed by Gallios flow cytometer (Beckman Coulter, Brea, CA, USA). Apoptosis detection was performed by FITC Annexin V/PI commercial kit (Becton Dickenson, Franklin Lakes, N.J., USA) following the manufacture protocol. The samples were analyzed by fluorescence-activated cell sorting (FACS) with a Gallios flow cytometer (Beckman Coulter, Brea, Calif., USA) within 1 h after staining Data were analyzed using Kaluzav 1.2 (Beckman Coulter). The results of this study are presented in Table 5, FIG. 13.

TABLE 5

Cell cycle analysis of compounds 4b and 4j

| Compound No | % G0-G1 | % S | % G2/M | % Pre-G1 |
|---|---|---|---|---|
| 4b | 45.26 | 36.71 | 18.03 | 24.33 |
| 4j | 36.99 | 31.84 | 31.17 | 34.52 |
| Cont. MCF-7 | 53.89 | 41.08 | 5.03 | 1.43 |

Figure 12:
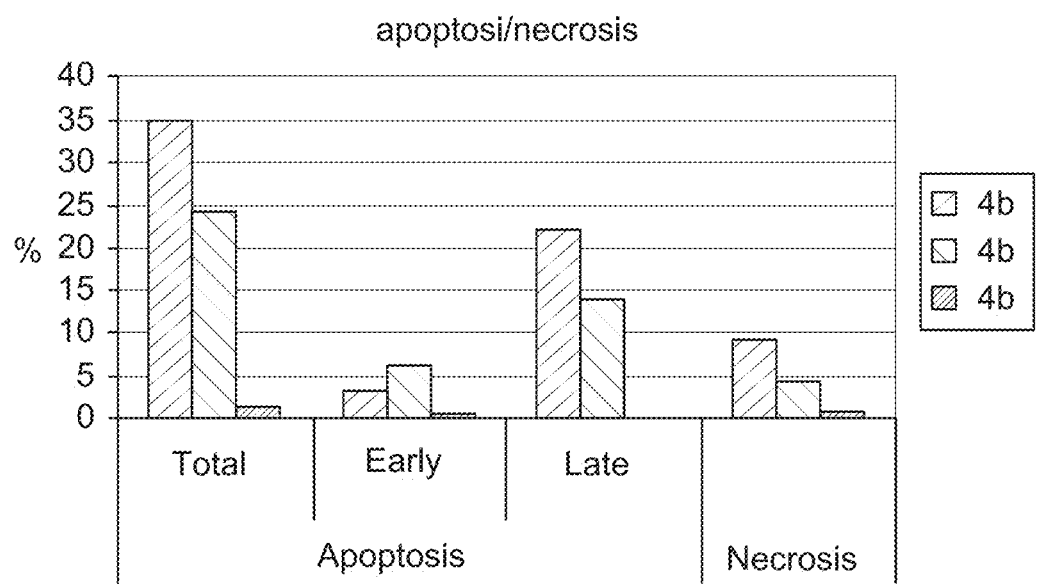
FIG. 12 shows apoptosis induction against MCF-7 cells caused by the derivatives 4b, and 4j.
Figure 13:
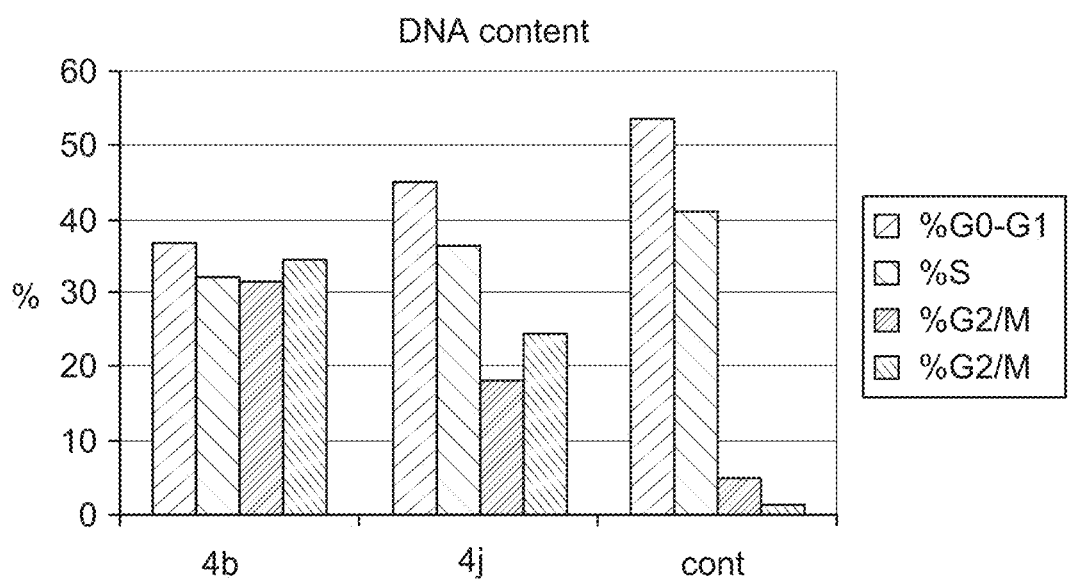
FIG. 13 shows cell cycle results of compounds 4b and 4j.

From a combined reading of Table 5 and FIG. 12, it can be observed that there was cell accumulation of percentages 24.33% and 18.03% at pre G1 and G2/M phases in MCF-7 cells treated with compound 4b, and cell accumulation percentages of 34.52% and 31.17% at pre G1 and G2/M phases in MCF-7 cells treated with compound 4j comparing to 1.43% and 5.03% of the untreated MCF-7 cells. This result represents that there was cell cycle arrest at G2/M phase with mitotic cycle cessation.

Molecular docking study

The molecular modelling studies were carried out using MOE (2019.0102) software. All minimizations were performed with MOE until an RMSD gradient of 0.1 kcal.mol$^{-1}$Å$^{-1}$ with MMFF94x force field, and the partial charges were automatically calculated.

Human epidermal growth factor receptor 2 (HER2)

Figure 14:
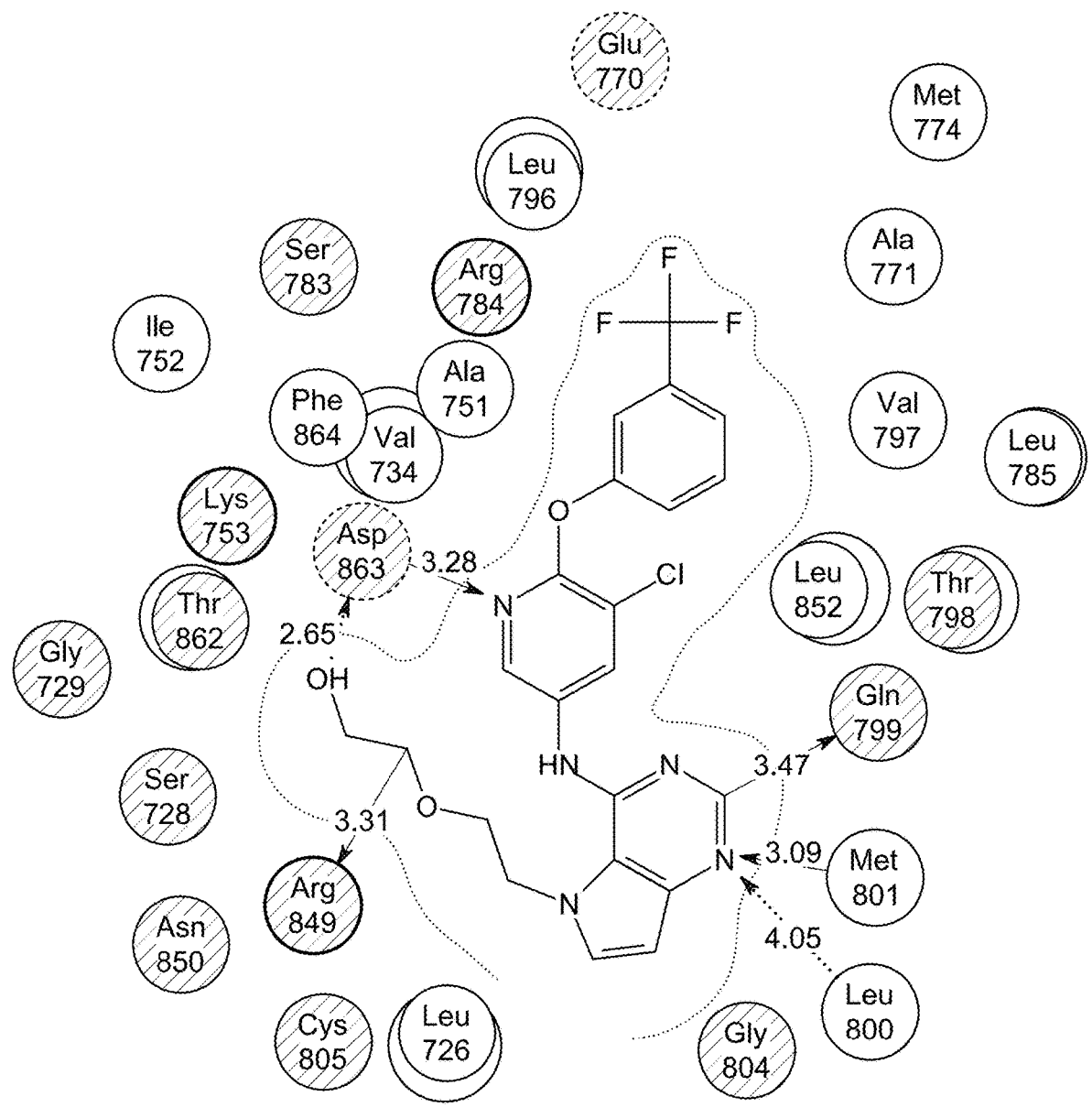
FIG. 14 shows 2D interactions of PDB ID: 3PP0 within HER2 active site.
Figure 15:
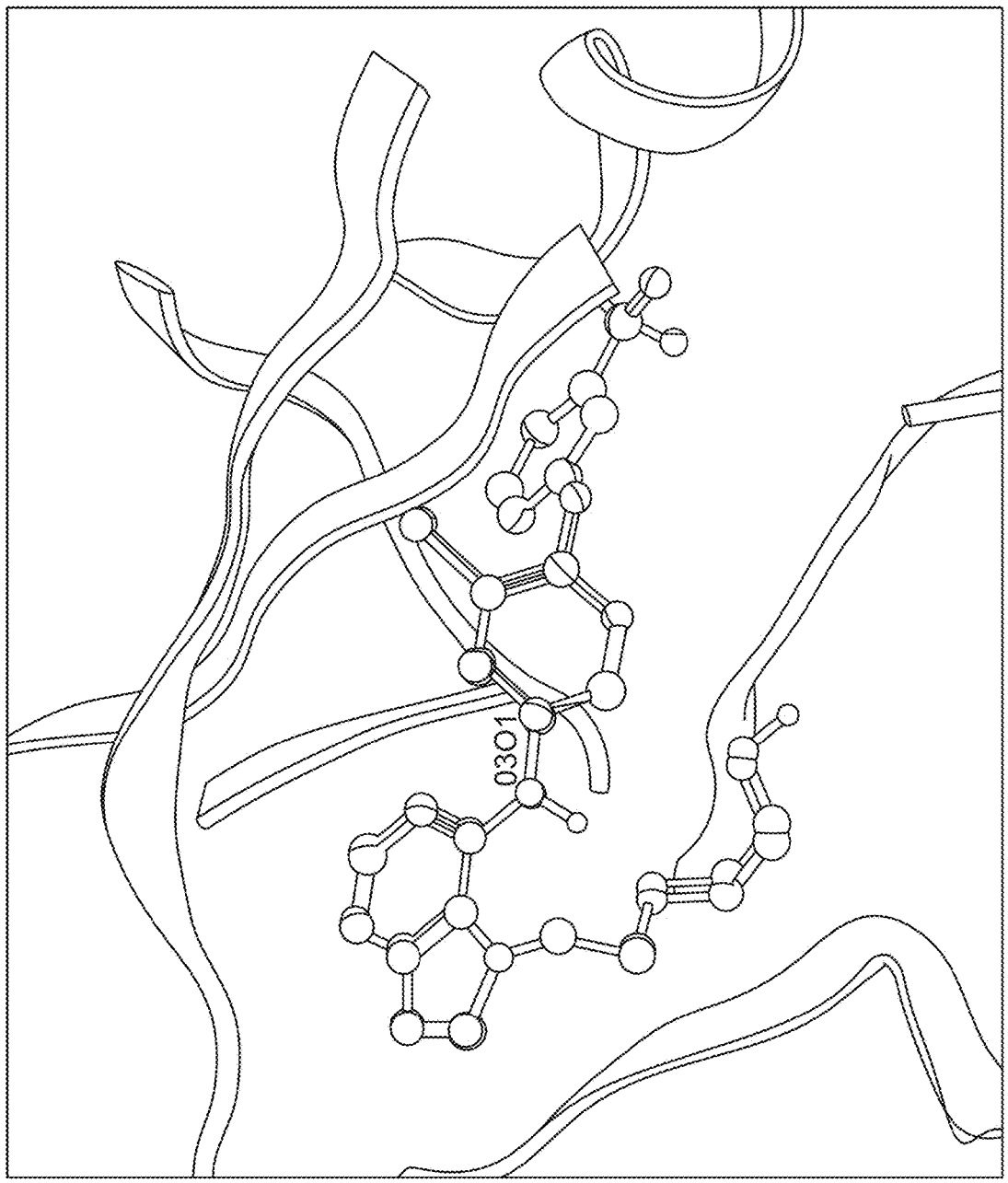
FIG. 15 shows 3D representation of the superimposition of the co-crystallised and the docking pose of PDB ID: 3PP0 in the active site of HER2.
Figure 16A:
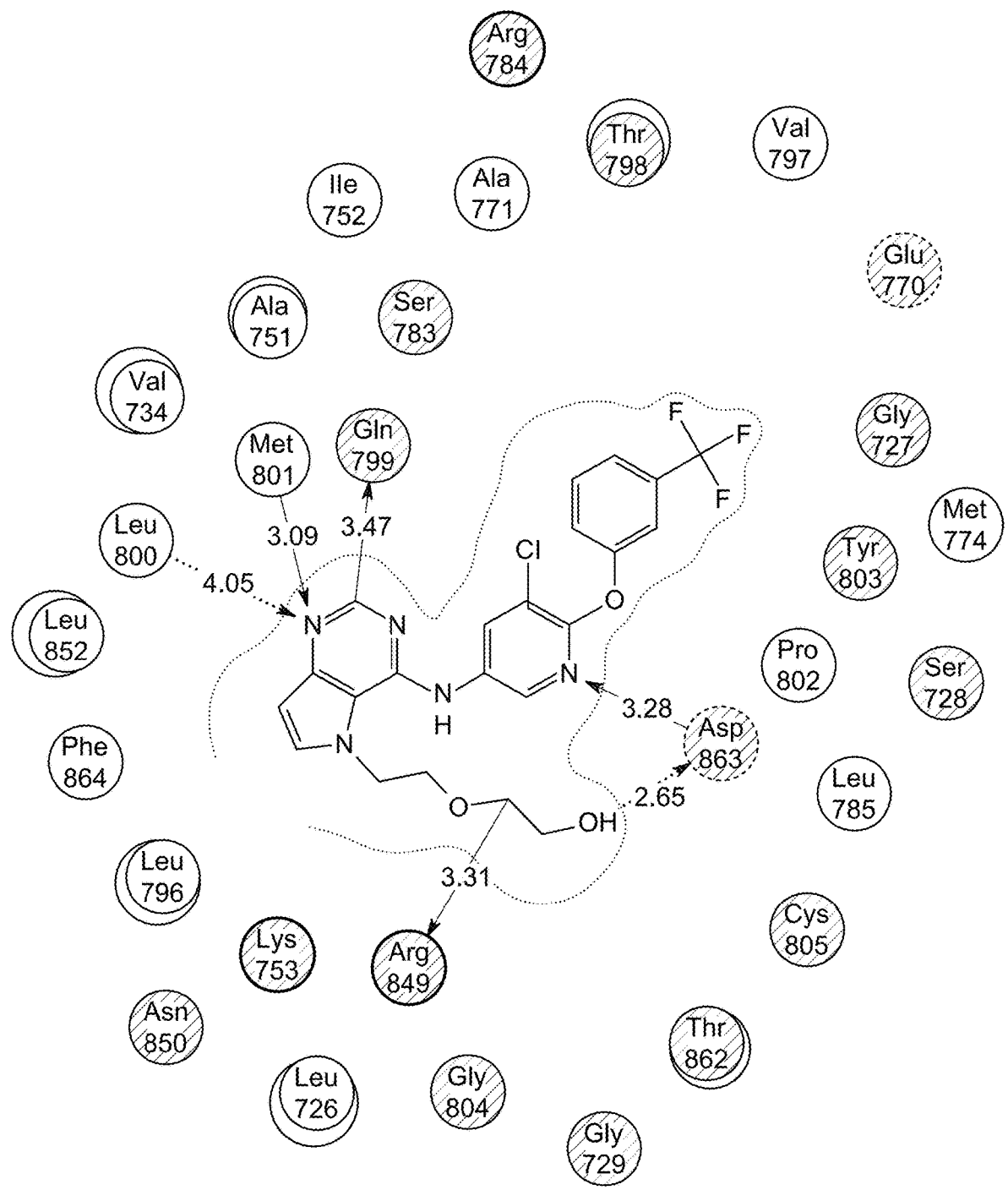
FIGS. 16A and 16B shows 2D and 3D diagram of compound 4j interactions within HER2 binding site.
Figure 16B:
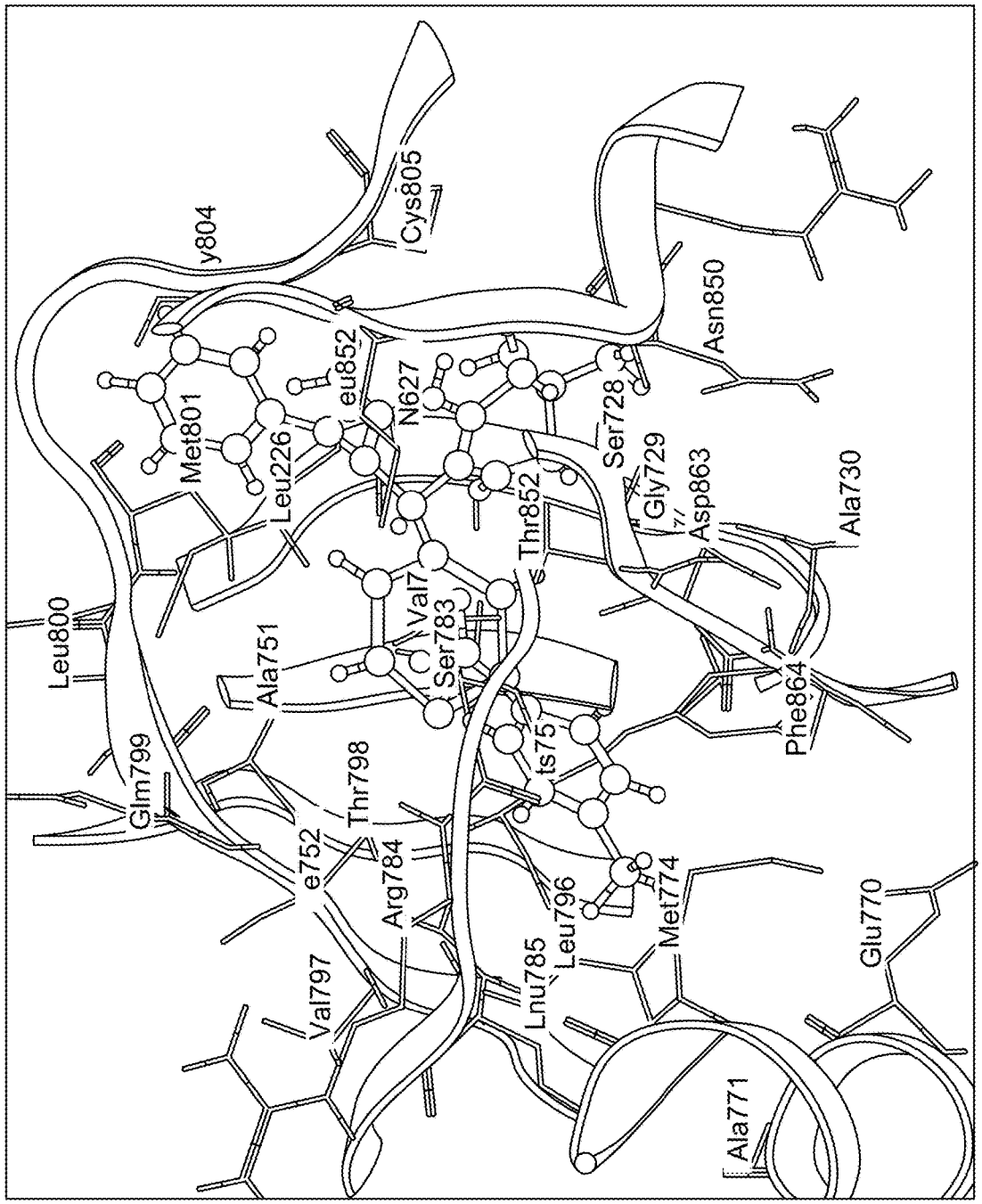
Figure 17A:
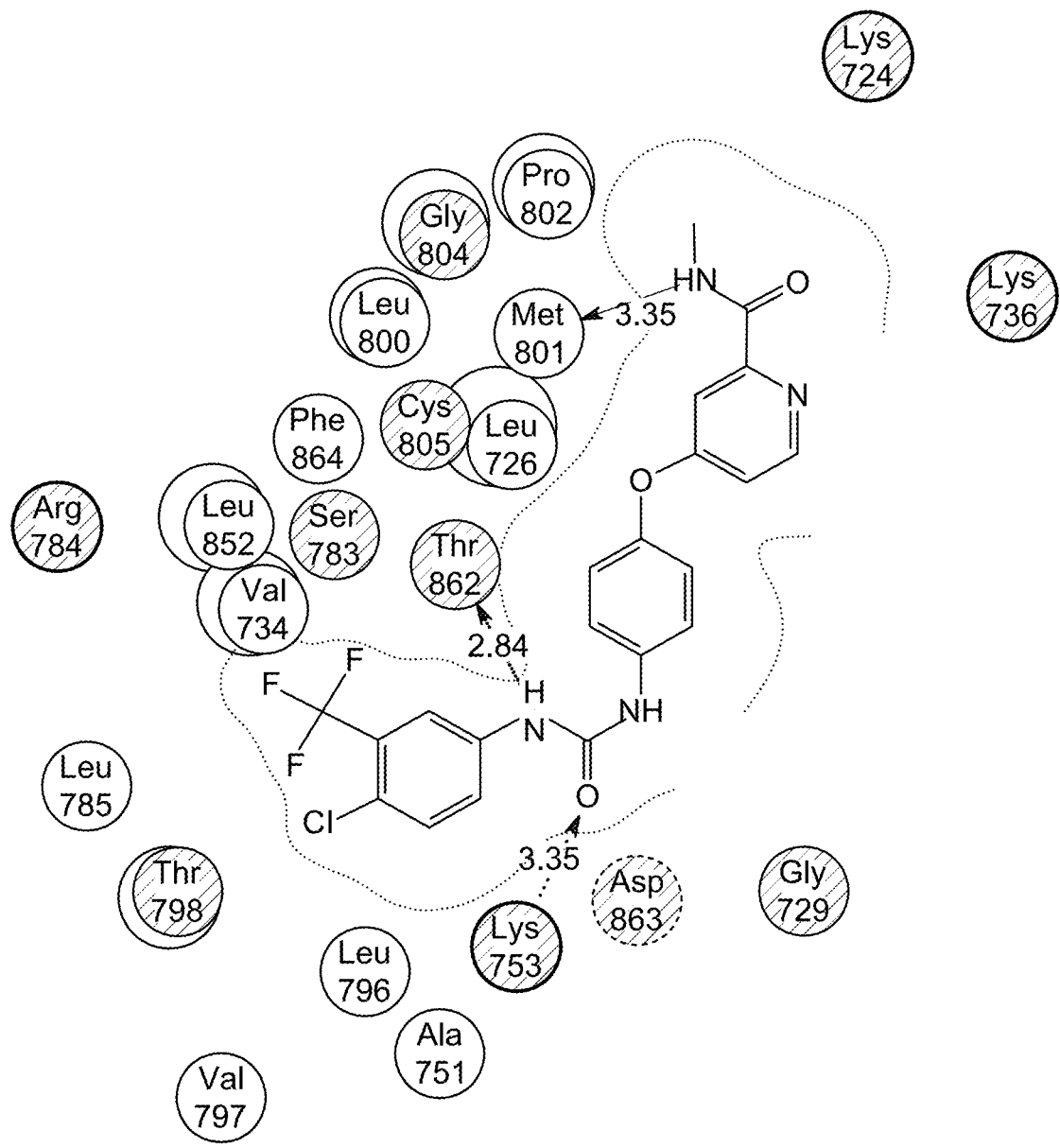
FIGS. 17A and 17B shows 2D and 3D diagram of compound Sorafenib interactions within HER2 binding site.
Figure 17B:
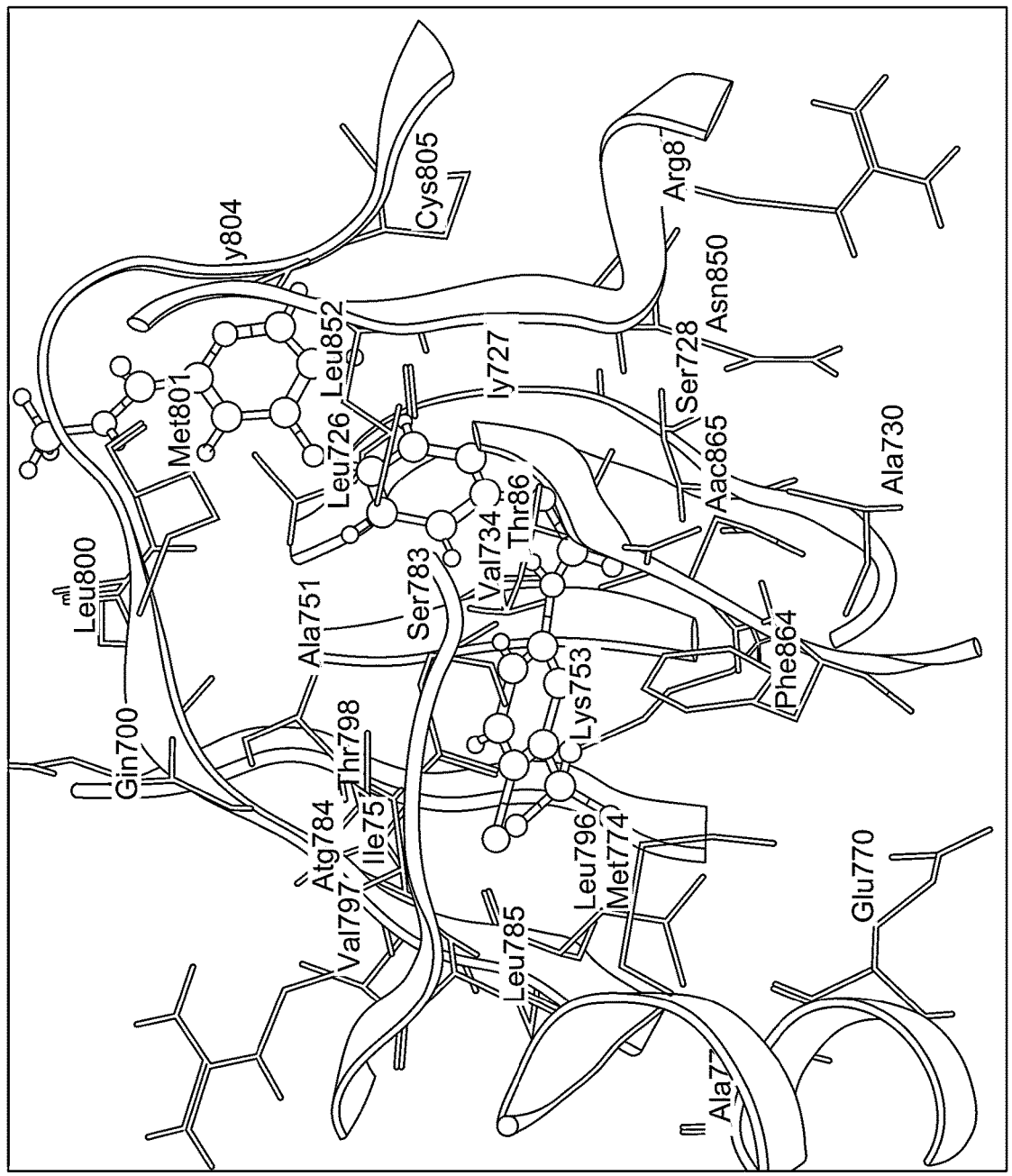

The X-ray crystallographic structure of human HER2 (HER2) co-crystalized with 2-f2-[4-(f5-chloro-6-[3 (trifluoromethyl)phenoxy]-pyridin-3-ylgamino)-5H-pyrrolo[3,2-d]pyrimidin-5-yl]ethoxygethanol (03Q) (PDB ID: 3PP0) was downloaded from the protein data bank (https://wwwscs-b.org/structure/3PP0). For each co-crystallized enzyme, water molecules and ligands that are not involved in the binding were removed. The protein was prepared for the docking study using Protonate 3D protocol in MOE with default options. The co-crystallized ligand (03Q) was used to define the binding site for docking. Triangle Matcher placement method and London dG scoring function were used for docking. Through examination of the binding interactions of 03Q to the active site of the enzyme, it shows strong bond interactions with Gln799, Leu800, Met801, Arg849, and Asp863 (FIG. 14). The docking setup was first validated by self-docking the co-crystallized ligand (30Q) in the vicinity of the enzyme's binding site. The docking score (S) was -17.1413 kcal/mol, and the root means square deviation (RMSD) was 0.14339 Å (FIG. 15). The 4j compound showed high energy binding score (-17.3597 kcal/mol.) like that of the co-crystallized ligand and higher than sorafenib. Moreover, it showed good binding interactions with the amino acids in the active site of the receptor. The results are summarized in Table 6 and FIG. 16A, FIG. 16B, and FIG. 17A and FIG. 17B.

TABLE 6

Docking data of compound 4j in the active site of HER2

| Compound | S (kcal/mol) | Amino acids | Interacting groups | Type of interaction | Length (A°) |
|---|---|---|---|---|---|
| 4j | -17.3597 | Gln799 | CH (Pyrimidine) | Electrostatic | 3.47 |
|  |  | Leu800 | N (Pyrimidine) | H-bond acceptor | 4.05 |
|  |  | Met801 | N (Pyrimidine) | H-bond acceptor | 3.09 |
|  |  | Arg849 | CH$_2$ | Electrostatic | 3.31 |
|  |  | Asp863 | OH | H-bond donor | 2.65 |
|  |  | Asp863 | N (Pyridine) | H-bond acceptor | 3.28 |
| Sorafenib | -15.4085 | Lys753 | O (C=O) | H-bond acceptor | 3.35 |
|  |  | Met801 | NH (amide) | H-bond donor | 3.25 |
|  |  | Thr862 | NH (Urea) | H-bond donor | 2.84 |

Platelet-derived growth factor receptor-a (PDGFR-α)

Figure 18:
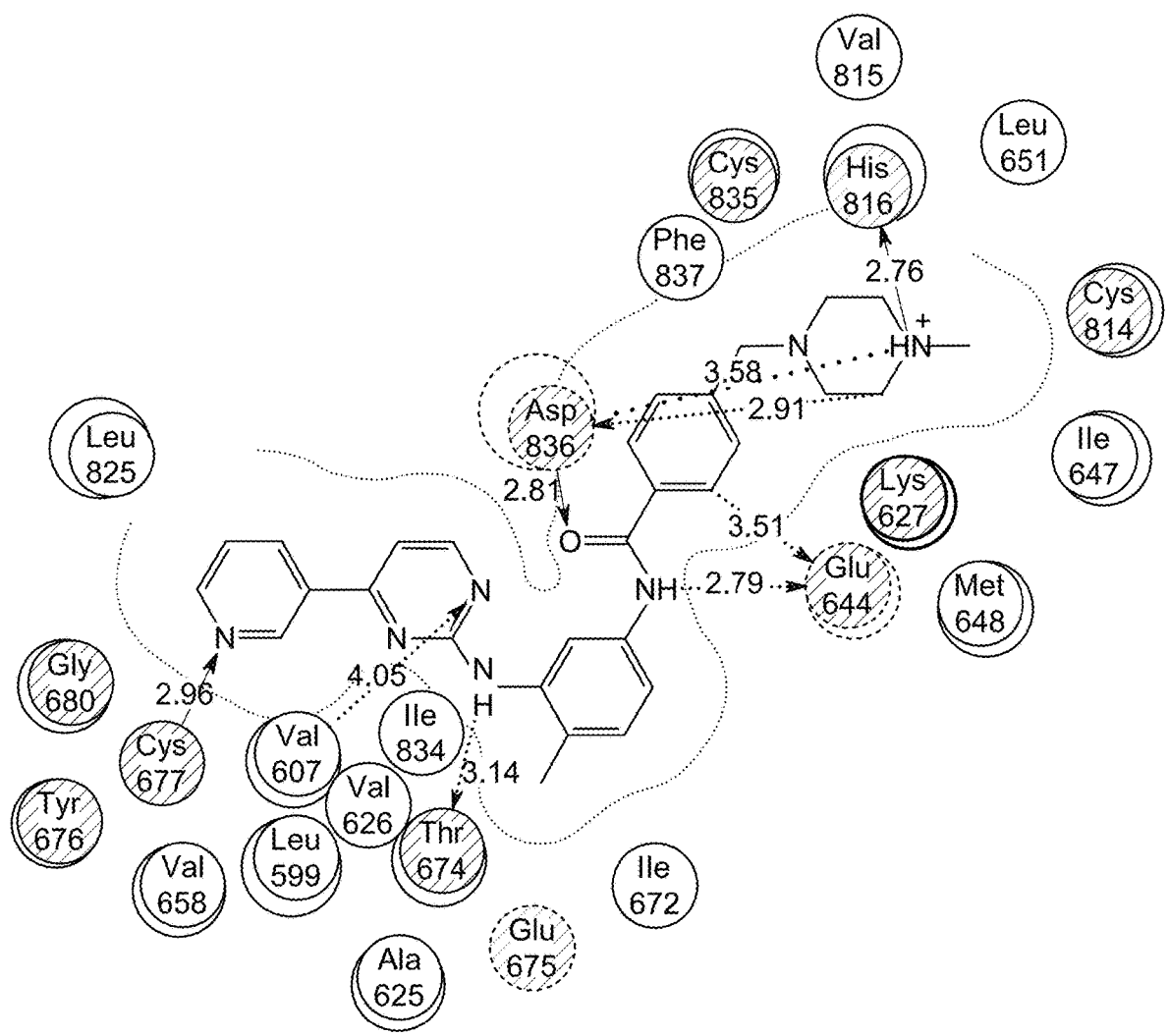
FIG. 18 shows 2D interactions of imatinib within PDGFR-α active site.
Figure 19:
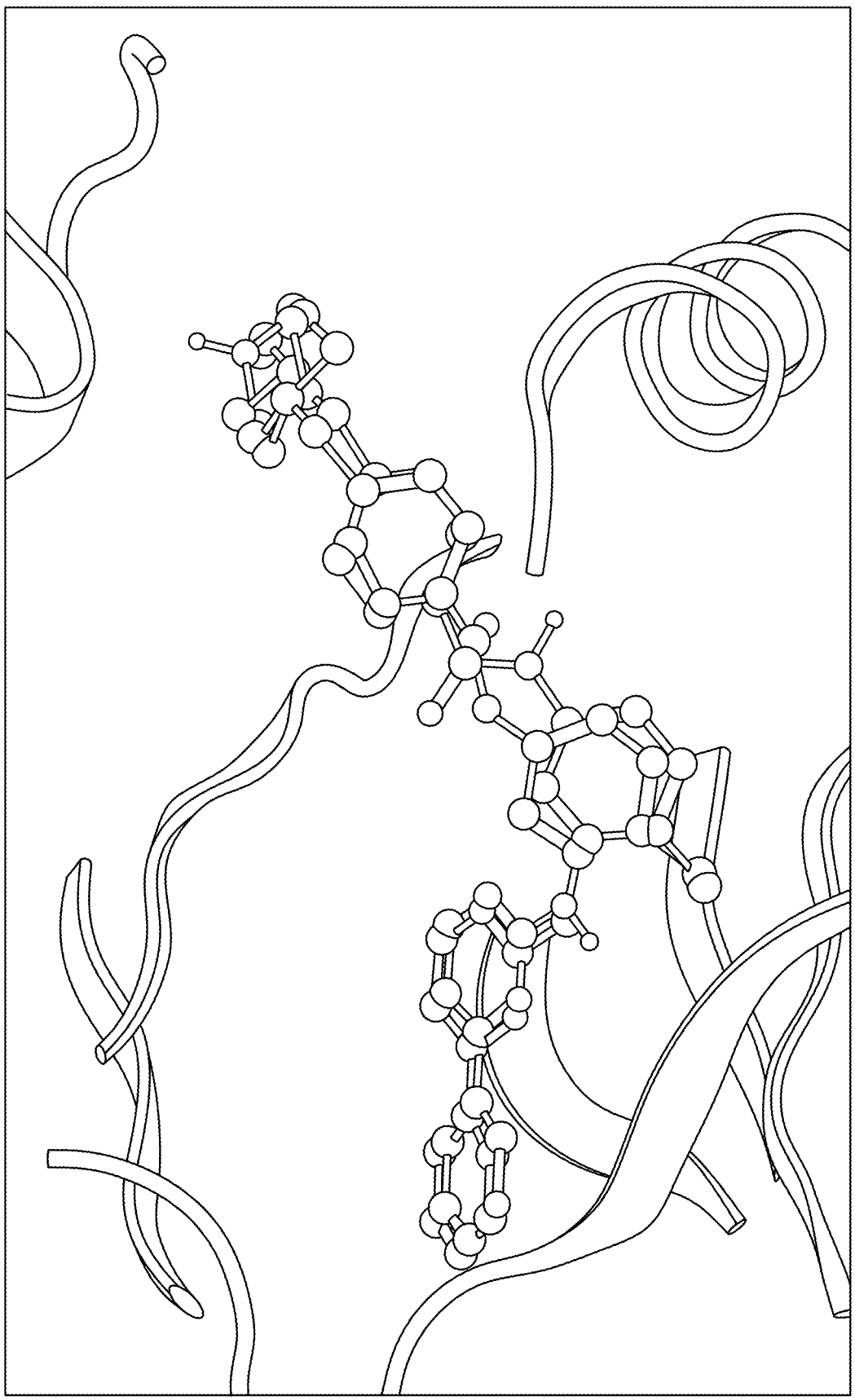
FIG. 19 shows 3D representation of the superimposition of the co-crystallised and the docking pose of imatinib in the active site of PDGFR-α.
Figure 20A:
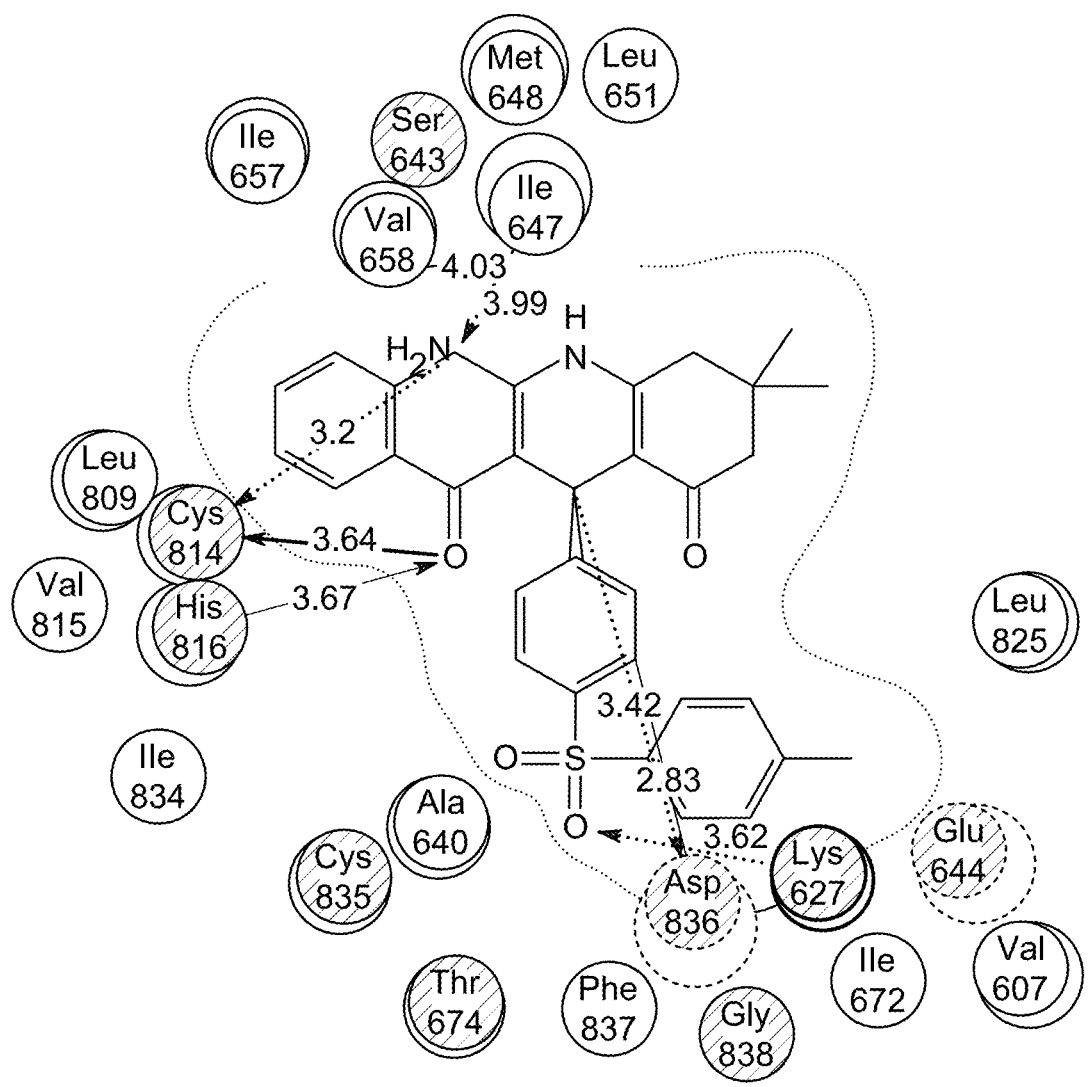
FIG. 20A is a 2D diagram of Sorafenib interactions within PDGFR-α binding site.
Figure 20B:
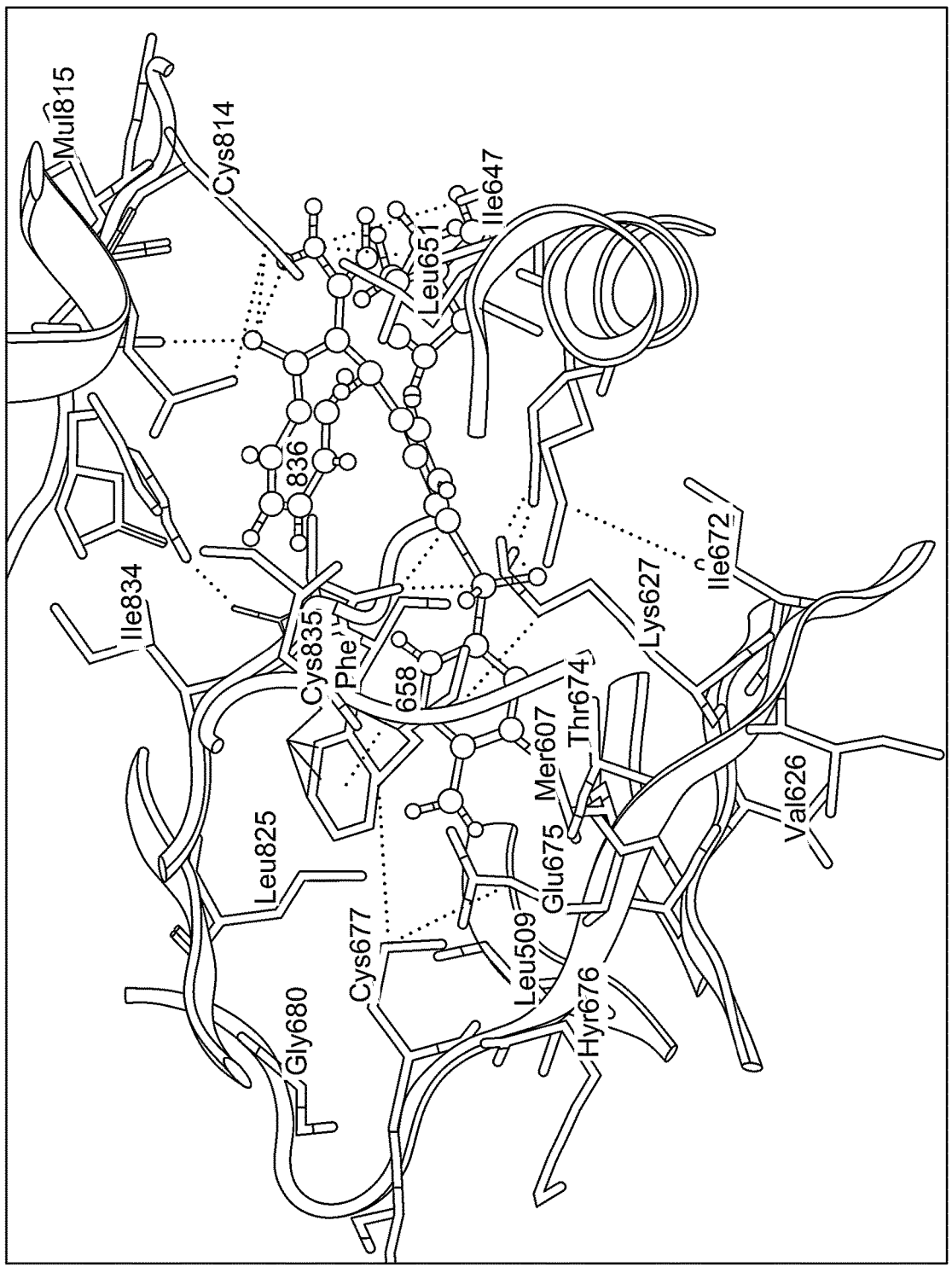
FIG. 20B is a 3D diagram of Sorafenib interactions within PDGFR-α binding site.
Figure 21A:
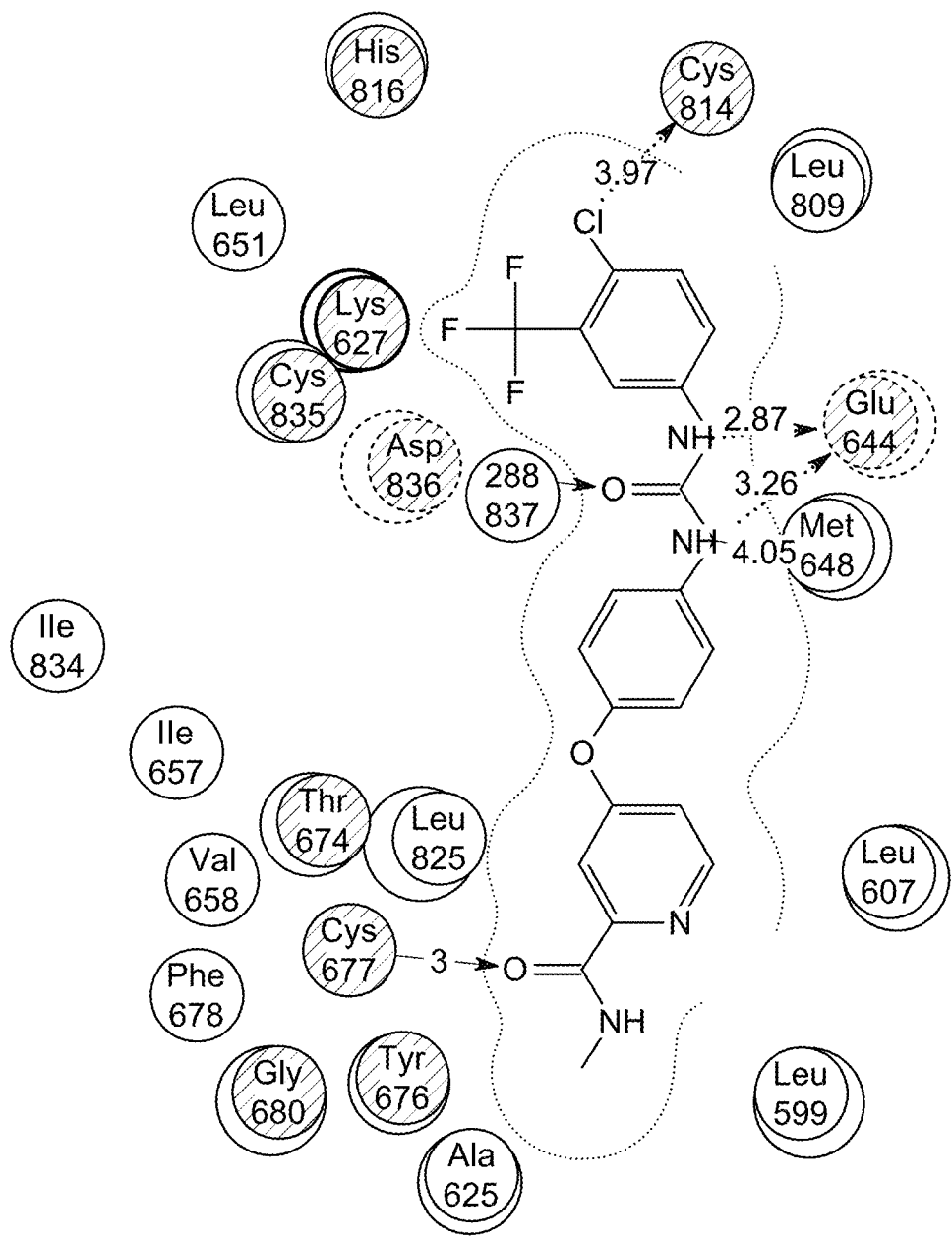
FIG. 21A is a 2D diagram of Sorafenib interactions within PDGFR-α binding site.
Figure 21B:
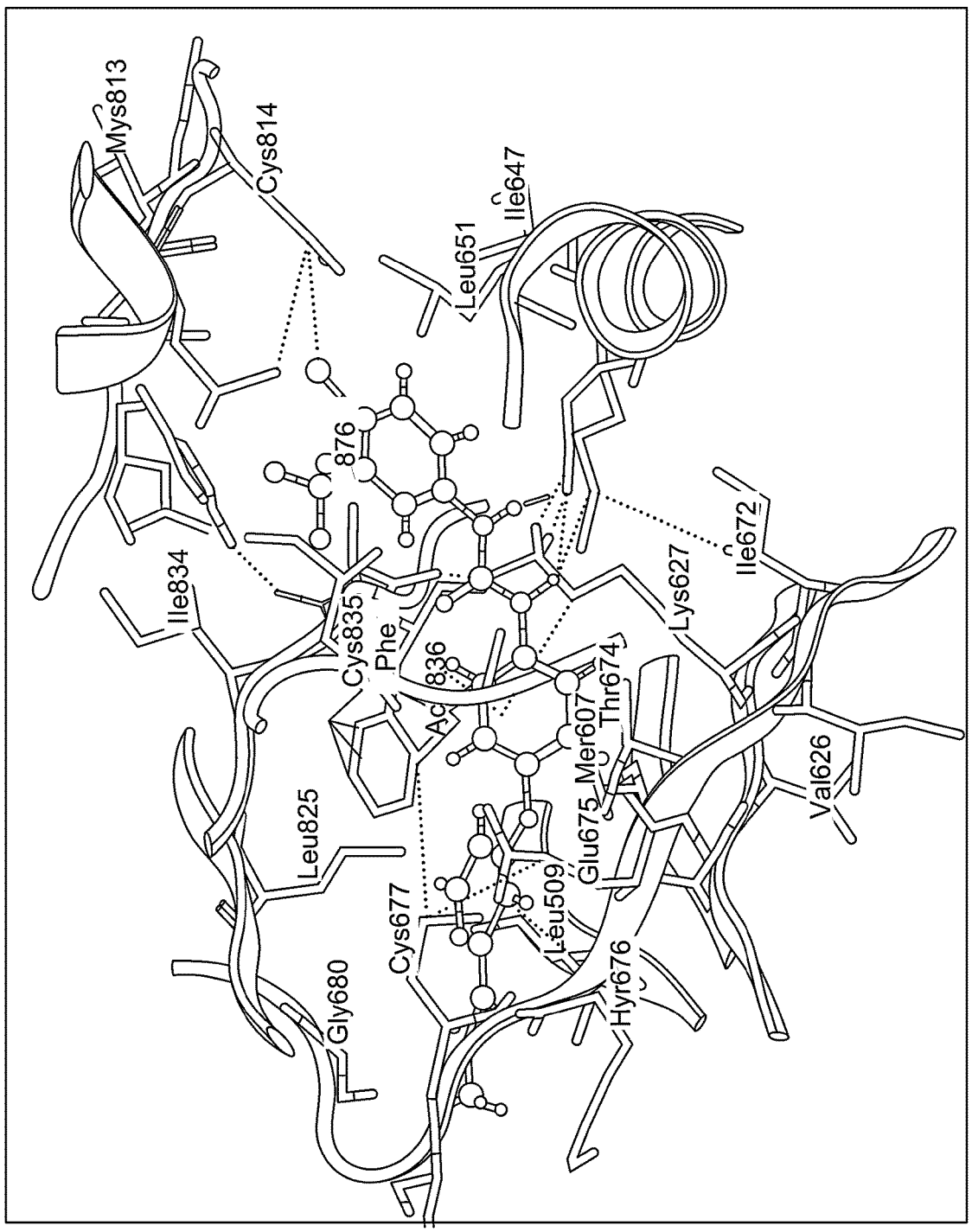
FIG. 21B is a 3D diagram of Sorafenib interactions within PDGFR-α binding site.

The X-ray crystallographic structure of human PDGFR-α co-crystalized with Imatinib (PDB ID: 6JOL) was downloaded from the protein data bank. For each co-crystallized enzyme, water molecules and ligands that are not involved in the binding were removed. The protein was prepared for the docking study using protonate 3D protocol in MOE with default options. The co-crystallized ligand (imatinib) was used to define the binding site for docking. Triangle Matcher placement method and London dG scoring function were used for docking. By examining the binding interactions of imatinib to the enzyme's active site, it shows strong bond interactions with Val607, Glu644, Thr674, Cys677, His816, and Asp836 (FIG. 18). The docking setup was first validated by self-docking the co-crystallized ligand (imatinib) in the vicinity of the enzyme's binding site. The docking score (S) was -18.0520 kcal/mol, and RMSD was 0.6983 Å (FIG. 19). The 4j compound showed a similar energy binding score to that of Sorafenib. It exhibited good binding interactions with the amino acid in PDGFR-α active site. The results are summarized in Table 7 and FIG. 20A, FIG. 20B, and FIG. 21A and FIG. 21B.

TABLE 7

Docking results of compound 4j in the active site of PDGFR-α.

| Compound | S (kcal/mol) | Amino acids | Interacting groups | Type of interaction | Length (A°) |
|---|---|---|---|---|---|
| 4j | -13.2171 | Lys627 | O (S=O) | H-bond acceptor | 3.62 |
|  |  | Ile647 | NH2 | H-bond acceptor | 3.99 |
|  |  | Cys814 | NH2 | H-bond donor | 3.2 |
|  |  | Cys814 | O (C=O) | Electrostatic | 3.64 |
|  |  | His816 | O (C=O) | H-bond acceptor | 3.67 |
|  |  | Asp836 | CH (phenyl) | Electrostatic | 2.83 |
|  |  | Asp836 | CH | Electrostatic | 3.42 |
| Sorafenib | -13.0476 | Glu644 | NH | H-bond donor | 2.87 |
|  |  | Glu644 | NH | H-bond donor | 3.26 |
|  |  | Met648 | NH | H-bond acceptor | 4.05 |
|  |  | Cys677 | O (C=O) | H-bond acceptor | 3 |
|  |  | Cys814 | Cl | Halogen bond | 3.97 |
|  |  | Asp836 | O (C=O) | H-bond acceptor | 2.88 |

INDUSTRIAL APPLICABILITY

The present disclosure provides a series of 4,6,7,8-tetrahydroquinolin-5(1H)-one-based derivatives has been synthesized as anti-breast cancer (MCF-7) agents of potential multi-targeting RTKs. From among the compounds evaluated for their cytotoxic activity, it was observed that compound 4j has shown potent multi-targeting inhibitory activity in comparison with Sorafenib. In addition, the biological evidence revealed that the compound 4j caused a marked apoptotic degree with a necrosis percentage 4.2%, leading to cell cycle disruption at G2/M phase in MCF-7 cancer cells. Accordingly, the new derivatives bearing 4,6,7,8-tetrahydroquinolin-5(1H)-one scaffold could be considered for further structural studies to get more potent, selective, and safer anticancer candidates. A molecular docking study was found in complete agreement with the obtained experimental results. Also, the green, synthetic process by which the compounds of the present disclosure are synthesized resulted in a significant reduction in reaction time from 5 to 6 h into 20-30 minutes, with an increase in yield to 90-95% from 78-84% under conventional conditions.

It is understood that the examples, embodiments, and teachings presented in this application are described merely for illustrative purposes. Any variations or modifications thereof are to be included within the scope of the present application as discussed.

What is claimed is:

1. A compound of Formula (I) and isomers and pharmaceutically acceptable salts thereof:

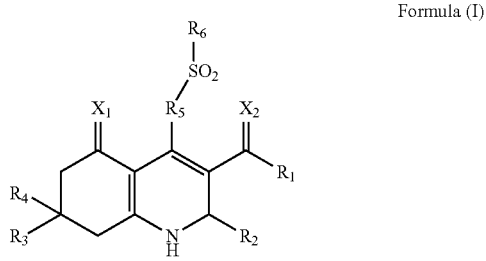

Formula (I)

wherein $X_1$ and $X_2$ each, independently, are oxygen or sulphur;
$R_1$ is a lower alkoxy, or an optionally substituted aryl group;
$R_2$ is selected from a group consisting of hydrogen, lower alkyl, haloalkyl, and an amino group;
$R_3$ and $R_4$ each, independently, are hydrogen, or lower alkyl groups; and
$R_5$ and $R_6$ are optionally substituted aryl groups.

2. The compound according to claim 1, wherein $X_1$ and $X_2$ are oxygen.

3. The compound according to claim 1, wherein $R_1$ is a methoxy or an ethoxy group.

4. The compound according to claim 1, wherein $R_1$ is an aryl group substituted with at least one substituent selected from a group consisting of a lower alkyl, haloalkyl, and a halogen.

5. The compound according to claim 1, wherein Ri is an aryl group substituted with a methyl group or a halogen.

6. The compound according to claim 5, wherein the aryl group is a phenyl group.

7. The compound according to claim 5, wherein the halogen is bromine.

8. The compound according to claim 1, wherein each of $R_3$ and $R_4$ is a methyl group.

9. The compound according to claim 1, wherein $R_5$ is a phenyl group.

10. The compound according to claim 1, wherein $R_6$ is a phenyl or a tolyl group.

11. The compound according to claim 1 further comprising, a compound of Formula (II) and isomers and pharmaceutically acceptable salts thereof.

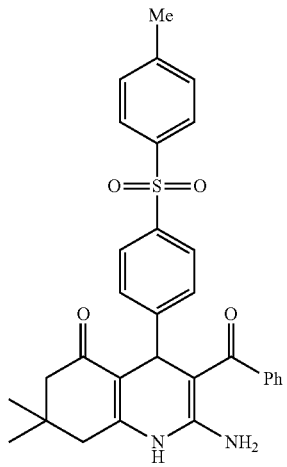

Formula (II)

12. A pharmaceutical composition comprising the compound of Formula (I) according to claim 1, and at least one pharmaceutically acceptable excipient selected from a group consisting of disintegrators, binders, fillers, lubricants, and any combination thereof.

* * * * *